(12) United States Patent
Karlin et al.

(10) Patent No.: US 8,173,686 B2
(45) Date of Patent: *May 8, 2012

(54) USE OF PICOPLATIN TO TREAT COLORECTAL CANCER

(75) Inventors: David A. Karlin, Los Altos, CA (US); Hazel B. Breitz, Seattle, WA (US); Paul L. Weiden, Seattle, WA (US)

(73) Assignee: Poniard Pharmaceuticals, Inc., Seattle, WA (US)

( * ) Notice: Subject to any disclaimer, the term of this patent is extended or adjusted under 35 U.S.C. 154(b) by 165 days.

This patent is subject to a terminal disclaimer.

(21) Appl. No.: 12/465,563

(22) Filed: May 13, 2009

(65) Prior Publication Data

US 2009/0306034 A1 Dec. 10, 2009

Related U.S. Application Data

(63) Continuation-in-part of application No. 12/367,394, filed on Feb. 6, 2009, which is a continuation-in-part of application No. 11/982,841, filed on Nov. 5, 2007, now abandoned.

(60) Provisional application No. 60/857,066, filed on Nov. 6, 2006, provisional application No. 60/857,725, filed on Nov. 8, 2006, provisional application No. 60/877,495, filed on Dec. 28, 2006, provisional application No. 60/889,191, filed on Feb. 9, 2007, provisional application No. 60/931,589, filed on May 24, 2007, provisional application No. 60/983,852, filed on Oct. 30, 2007.

(51) Int. Cl.
*A61K 31/44* (2006.01)

(52) U.S. Cl. ........................................ 514/357

(58) Field of Classification Search .................. None
See application file for complete search history.

(56) References Cited

U.S. PATENT DOCUMENTS

| | | | |
|---|---|---|---|
| 3,892,790 A | 7/1975 | Tobe et al. |
| 4,322,391 A | 3/1982 | Murray et al. |
| 4,329,299 A | 5/1982 | Hydes |
| 4,394,319 A | 7/1983 | Hydes |
| 4,419,340 A | 12/1983 | Yolles |
| 4,533,502 A | 8/1985 | Rochon et al. |
| 4,760,155 A | 7/1988 | Heffernan et al. |
| 4,902,797 A | 2/1990 | Totani et al. |
| 5,072,011 A | 12/1991 | Abrams et al. |
| 5,082,655 A | 1/1992 | Snipes et al. |
| 5,194,645 A | 3/1993 | Barnard |
| 5,244,991 A | 9/1993 | Abrams et al. |
| 5,519,155 A | 5/1996 | Barnard et al. |
| 5,595,979 A | 1/1997 | Snyder |
| 5,624,919 A | 4/1997 | Farrell |
| 5,626,862 A | 5/1997 | Brem et al. |
| 5,633,016 A | 5/1997 | Johnson |
| 5,665,771 A | 9/1997 | Murrer |
| 5,681,582 A | 10/1997 | Gilis et al. |
| 5,795,589 A | 8/1998 | Mayer et al. |
| 5,919,815 A | 7/1999 | Bradley et al. |
| 5,976,577 A | 11/1999 | Green et al. |
| 6,177,251 B1 | 1/2001 | Vogelstein et al. |
| 6,235,782 B1 | 5/2001 | Pamukcu et al. |
| 6,245,349 B1 | 6/2001 | Yiv et al. |
| 6,413,953 B1 | 7/2002 | Gianomenico et al. |
| 6,518,428 B1 | 2/2003 | Wong et al. |
| 6,544,961 B1 | 4/2003 | St. Clair et al. |
| 6,544,962 B1 | 4/2003 | Jones et al. |
| 6,673,370 B2 | 1/2004 | Burke et al. |
| 6,699,844 B2 | 3/2004 | Jones et al. |
| 6,774,131 B1 | 8/2004 | Yuyama et al. |
| 6,806,289 B1 | 10/2004 | Lippard et al. |
| 6,884,817 B2 | 4/2005 | Li et al. |
| 6,894,049 B1 | 5/2005 | Wong |
| 6,906,048 B2 | 6/2005 | Davis et al. |
| 7,011,851 B2 | 3/2006 | Burke et al. |
| 7,109,337 B2 | 9/2006 | Kath et al. |
| 7,122,668 B2 | 10/2006 | Barenholz et al. |
| 7,145,008 B2 | 12/2006 | Kath et al. |
| 7,201,913 B1 | 4/2007 | Muggetti et al. |
| 7,208,499 B2 | 4/2007 | Kath et al. |
| 7,235,562 B2 | 6/2007 | Kath et al. |
| 7,253,209 B2 | 8/2007 | Kishimoto et al. |
| 7,262,182 B2 | 8/2007 | Robinson et al. |
| 7,264,798 B2 | 9/2007 | Cofey et al. |
| 7,265,134 B2 | 9/2007 | Hartman et al. |
| 7,307,100 B2 | 12/2007 | Mujica-Fernaud et al. |
| 7,354,945 B2 | 4/2008 | Mujica-Fernaud et al. |
| 7,378,421 B2 | 5/2008 | Mujica-Fernaud et al. |
| 7,378,423 B2 | 5/2008 | Kawasaki et al. |
| 7,390,799 B2 | 6/2008 | Bruncko et al. |
| 2002/0102301 A1 | 8/2002 | Schwarz |

(Continued)

FOREIGN PATENT DOCUMENTS

CN 1857208 A 11/2006

(Continued)

OTHER PUBLICATIONS

"U.S. Appl. No. 10/276,503, Non Final Office Action mailed Sep. 9, 2010", 24 pgs.

"U.S. Appl. No. 10/276,503, Response filed Dec. 9, 2010 to Non Final Office Action mailed Sep. 9, 2010", 16 pgs.

"U.S. Appl. No. 11/935,979 Non-Final Office Action mailed Oct. 4, 2010", 10 pgs.

"U.S. Appl. No. 11/935,979, Advisory Action mailed Aug. 23, 2010", 3 pgs.

"U.S. Appl. No. 11/935,979, Examiner Interview Summary Received Dec. 16, 2010", 3 pgs.

"U.S. Appl. No. 11/935,979, Examiner Interview Summary Received Jun. 28, 2010", 3 pgs.

"U.S. Appl. No. 11/935,979, Final Office Action mailed Jan. 7, 2011", 12 pgs.

"U.S. Appl. No. 11/935,979, Response filed Jan. 25, 2011 to Final Office Action mailed Jan. 7, 2011 and Advisory Action mailed Jan. 21, 2011", 52 pgs.

(Continued)

*Primary Examiner* — James D Anderson

(74) *Attorney, Agent, or Firm* — Schwegman, Lundberg & Woessner, P.A.

(57) ABSTRACT

The invention provides a method of treatment of colorectal cancer by administration of the anti-cancer platinum drug picoplatin in conjunction with 5-FU and leucovorin in a variety of treatment regimens.

18 Claims, No Drawings

U.S. PATENT DOCUMENTS

| | | |
|---|---|---|
| 2002/0110601 A1 | 8/2002 | Perez-Soler et al. |
| 2002/0156033 A1 | 10/2002 | Bratzler et al. |
| 2002/0187191 A1 | 12/2002 | Burke et al. |
| 2002/0193362 A1 | 12/2002 | Morinaga et al. |
| 2002/0193434 A1 | 12/2002 | Morinaga et al. |
| 2003/0027808 A1 | 2/2003 | Palmer et al. |
| 2003/0108606 A1 | 6/2003 | Norden et al. |
| 2003/0109487 A1 | 6/2003 | Jones et al. |
| 2003/0118667 A1 | 6/2003 | Bissery |
| 2003/0144312 A1 | 7/2003 | Schoenhard |
| 2004/0010553 A1 | 1/2004 | Katz et al. |
| 2004/0033997 A1 | 2/2004 | Baron |
| 2004/0053882 A1 | 3/2004 | Smith et al. |
| 2004/0101553 A1 | 5/2004 | Lee et al. |
| 2004/0138140 A1 | 7/2004 | Xu et al. |
| 2004/0156816 A1 | 8/2004 | Anderson et al. |
| 2004/0229843 A1 | 11/2004 | Toole et al. |
| 2005/0009908 A1 | 1/2005 | Hedberg et al. |
| 2005/0020556 A1 | 1/2005 | Johnson et al. |
| 2005/0026896 A1 | 2/2005 | Keppler |
| 2005/0107346 A1 | 5/2005 | Davis et al. |
| 2005/0232952 A1 | 10/2005 | Lambert et al. |
| 2005/0249822 A1 | 11/2005 | Pilkiewicz et al. |
| 2005/0261202 A1 | 11/2005 | Brown et al. |
| 2005/0267075 A1 | 12/2005 | Allen et al. |
| 2006/0003950 A1 | 1/2006 | Strugnell et al. |
| 2006/0014768 A1 | 1/2006 | Kawasaki et al. |
| 2006/0058311 A1 | 3/2006 | Munzert et al. |
| 2006/0074073 A1 | 4/2006 | Steinfeldt et al. |
| 2006/0078618 A1 | 4/2006 | Constantinides et al. |
| 2006/0084670 A1 | 4/2006 | Bissery |
| 2006/0142593 A1 | 6/2006 | Lal |
| 2006/0183728 A1 | 8/2006 | Kelly |
| 2006/0205810 A1 | 9/2006 | Zong et al. |
| 2006/0211617 A1 | 9/2006 | Gulati |
| 2006/0211639 A1 | 9/2006 | Bratzler et al. |
| 2006/0246124 A1 | 11/2006 | Pilkiewicz et al. |
| 2006/0257401 A1 | 11/2006 | Stassi et al. |
| 2006/0263346 A1 | 11/2006 | Leenders et al. |
| 2006/0263434 A1 | 11/2006 | Desai et al. |
| 2006/0293323 A1 | 12/2006 | Elliott et al. |
| 2007/0065522 A1 | 3/2007 | Pilkiewicz et al. |
| 2007/0082838 A1 | 4/2007 | De et al. |
| 2007/0116729 A1 | 5/2007 | Palepu et al. |
| 2007/0122350 A1 | 5/2007 | Pilkiewicz et al. |
| 2007/0123502 A1 | 5/2007 | Turkson et al. |
| 2007/0190180 A1 | 8/2007 | Pilkiewicz et al. |
| 2007/0190181 A1 | 8/2007 | Pilkiewicz et al. |
| 2007/0190182 A1 | 8/2007 | Pilkiewicz et al. |
| 2007/0219268 A1 | 9/2007 | Hausheer |
| 2007/0265277 A1 | 11/2007 | Jikyo et al. |
| 2007/0269539 A1 | 11/2007 | Marshall et al. |
| 2008/0146555 A1 | 6/2008 | Caligiuri et al. |
| 2008/0159980 A1 | 7/2008 | Xu et al. |
| 2008/0161252 A1 | 7/2008 | Reddy et al. |
| 2008/0166428 A1 | 7/2008 | Brown et al. |
| 2008/0193498 A1 | 8/2008 | Hausheer |
| 2009/0010878 A1 | 1/2009 | Holmlund |
| 2009/0047365 A1 | 2/2009 | Owa et al. |
| 2009/0061010 A1 | 3/2009 | Zale et al. |
| 2009/0197854 A1 | 8/2009 | Karlin et al. |
| 2009/0275549 A1 | 11/2009 | Karlin et al. |
| 2010/0062056 A1 | 3/2010 | Leigh |
| 2010/0178328 A1 | 7/2010 | Martell et al. |
| 2010/0215727 A1 | 8/2010 | Leigh et al. |
| 2010/0310661 A1 | 12/2010 | Chen et al. |
| 2011/0033528 A1 | 2/2011 | Leigh et al. |
| 2011/0052580 A1 | 3/2011 | Martell et al. |
| 2011/0052581 A1 | 3/2011 | Karlin et al. |
| 2011/0053879 A1 | 3/2011 | Martell et al. |

FOREIGN PATENT DOCUMENTS

| | | |
|---|---|---|
| CN | 1857221 A | 11/2006 |
| CN | 1861050 A | 11/2006 |
| CN | 1861051 A | 11/2006 |
| CN | 1861052 A | 11/2006 |
| CN | 1861053 A | 11/2006 |
| CN | 1861054 A | 11/2006 |
| CN | 1861055 A | 11/2006 |
| CN | 1868452 A | 11/2006 |
| CN | 1868453 A | 11/2006 |
| CN | 1868454 A | 11/2006 |
| CN | 1957913 A | 5/2007 |
| CN | 101380303 A | 3/2009 |
| EP | 0115929 A1 | 8/1984 |
| EP | 0199524 B1 | 10/1986 |
| EP | 03333351 B1 | 9/1989 |
| JP | 7-501079 A | 2/1995 |
| WO | WO-99/56742 A1 | 11/1999 |
| WO | 0129235 | 4/2001 |
| WO | WO-01/74368 A1 | 10/2001 |
| WO | WO-02/085386 A2 | 10/2002 |
| WO | WO-03/041645 A2 | 5/2003 |
| WO | WO-03/103596 A2 | 12/2003 |
| WO | WO-2004/045593 A2 | 6/2004 |
| WO | WO-2006/104668 A2 | 10/2006 |
| WO | WO-2006/112777 A2 | 10/2006 |
| WO | WO-2008/097658 A1 | 8/2008 |
| WO | WO-2008/097661 A1 | 8/2008 |
| WO | WO-2009/011861 A1 | 1/2009 |
| WO | WO-2009/032034 A2 | 3/2009 |
| WO | WO-2009/076170 A2 | 6/2009 |
| WO | WO-2009/099634 A2 | 8/2009 |
| WO | WO-2009/099649 A1 | 8/2009 |
| WO | WO-2009/099651 A1 | 8/2009 |
| WO | WO-2010132596 A1 | 11/2010 |
| WO | WO-2011109752 A1 | 9/2011 |

OTHER PUBLICATIONS

"U.S. Appl. No. 11/935,979, Response filed Jul. 21, 2010 to Advisory Action mailed Jul. 13, 2010 and Final Office Action mailed May 14, 2010", 14 pgs.

"U.S. Appl. No. 11/935,979, Response filed Aug. 25, 2010 to Advisory Actions mailed Jul. 13, 2010 and Aug. 23, 2010 and Final Office Action mailed May 14, 2010", 14 pgs.

"U.S. Appl. No. 11/935,979, Response filed Jan. 12, 2011 to Final Office Action mailed Jan. 7, 2011", 12 pgs.

"U.S. Appl. No. 11/935,979, Response filed Dec. 9, 2010 to Non Final Office Action mailed Oct. 4, 2010", 12 pgs.

"Indian Patent Application No. 5256/CHENP/2009", 5 pgs.

"Indian Patent Appliction No. 5257/CHENP/2009", 4 pgs.

"Japanese Patent Application No. 2009-549126", 21.

"Japanese Patent Application No. 2009-549128", 23.

"Other News to Note", Bioworld Today, 10(223)., AN: 1999:298178 NLDB (STN) TI: Other News to Note SO: Bioworld Today, (Nov. 22, 1999), vol. 10, 223. PB: American Health Consultants, (Nov. 22, 1999), 1 pg.

Adams, G. P., et al., "Monoclonal antibody therapy of cancer", Nat Biotechnol., 23(9), (Sep. 2005), 1147-57.

Bailar, J. C., et al., "Cancer undefeated", N Engl J Med., 336(22), (May 29, 1997), 1569-74.

Bergman, A. M, et al., "Synergistic interaction between cisplatin and gemcitabine in vitro", Clin Cancer Res., 2(3), (Mar. 1996), 521-30.

Chang, Alex, "Chemotherapy, chemoresistance and the changing treatment landscape for NSCLC.", Lung Cancer, 71(1), (Jan. 2011), 3-10.

Decker, S., et al., "Preclinical modeling of combination treatments: fantasy or requirement?", Ann N Y Acad Sci., 1059, (Nov. 2005), 61-9.

Devita, Jr., V. T, et al., "Combination versus single agent chemotherapy: a review of the basis for selection of drug treatment of cancer.", Cancer, 35(1), (Jan. 1975), 98-110.

Engblom, Pirjo, et al., "Carboplatin-paclitaxel- and carboplatin-docetaxel-induced cytotoxic effect in epithelial ovarian carcinoma in vitro", Cancer, 86(10), (Nov. 15, 1999), 2066-73.

Fiebiger, Wolfgang, et al., "In vitro cytotoxicity of novel platinum-based drugs and dichloroacetate against lung carcinoid cell lines", Clin Transl Oncol.,13(1), (Jan. 2011), 43-9.

Haines, I. E, et al., "Perspective on "Chemotherapy for advanced prostate cancer: 25 years later": is it a mirage or an oasis?", J Clin Oncol., 26(24), (Aug. 20, 2008), 4049-50.

Jekunen, A. P., et al., "Synergistic interaction between cisplatin and taxol in human ovarian carcinoma cells in vitro", Br J Cancer., 69(2), (Feb. 1994), 299-306.

Lane, D., "Designer combination therapy for cancer.", Nat Biotechnol., 24(2), (Feb. 2006), 163-4.

Martel, C. L, et al., "Current strategies in the management of hormone refractory prostate cancer.", Cancer Treat Rev., 29(3), (Jun. 2003), 171-87.

Nakajima, Kuninobu, et al., "Characterization of two independent, exposure-time dependent paclitaxel-resistant human ovarian carcinoma cell lines", Hum Cell., 23(4), (Nov. 2010), 156-63.

Olszewski, U., et al., "A better platinum-based anticancer drug yet to come?", Anticancer Agents Med Chem.,10(4), (May 1, 2010), 293-301.

Poniard Press Release, "Poniard Pharmaceuticals Awarded $244,479 Grant Under Qualifying Therapeutic Discovery Project Programaml", Press Release—Nov. 4, 2010, 1.

Romond, E. H, et al., "Trastuzumab plus adjuvant chemotherapy for operable HER2-positive breast cancer.", N Engl J Med., 353(16), (Oct. 20, 2005), 1673-84.

Rougier, P., et al., "Metastatic colorectal cancer: first- and second-line treatment in 2005.", Semin Oncol., 32(6 Suppl 8), (Dec. 2005), 15-20.

Schrijvers, D., "Report—3rd Asia Pacific Lung Cancer Conference", European Society for Medical Oncology (ESMO) and International Association for the Study of Lung Cancer (IASLC), (2008), 9 pgs.

Tang, C, et al., "Picoplatin overcomes resistance to cell toxicity in small-cell lung cancer cells previously treatment with cisplatin and carboplatin.", Cancer Chemother Pharmacol (Published Online: Aug. 31, 2010), (2010), 12 pgs.

Wheate, N J, et al., "The status of platinum anticancer drugs in the clinic and in clinical trials.", Dalton Trans, 39:8113-8127, 2010., (2010), 8113-8127.

Zoli, W., et al., "In vitro preclinical models for a rational design of chemotherapy combinations in human tumors.", Crit Rev Oncol Hematol., 37(1), (Jan. 2001), 69-82.

"U.S. Appl. No. 11/935,979, Non-Final Office Action mailed Jan. 8, 2010", 8 pgs.

"U.S. Appl. No. 11/935,979, Response filed Feb. 26, 2010 to Non-Final Office Action mailed Jan. 8, 2010", 11 pgs.

"U.S. Appl. No. 11/935,979, Response filed Oct. 23, 2009 to Restriction Requirement mailed Sep. 21, 2009", 6 pgs.

"U.S. Appl. No. 11/935,979, Restriction Requirement mailed Sep. 21, 2009", 5 pgs.

"U.S. Appl. No. 11/982,839, Non-Final Office Action mailed Jan. 26, 2009", 10 pgs.

"U.S. Appl. No. 11/982,841, Non-Final Office Action mailed Jan. 27, 2009", 9 pgs.

"High Beam Research—Other News to Note", *BIOWORLD Today*, (Nov. 22, 1999), 2 pgs.

"International Application No. PCT/US2009/000750, International Search Report mailed on Apr. 17, 2009", 2 pgs.

"International Application No. PCT/US2009/000750, Written Opinion mailed on Apr. 17, 2009", 7 pgs.

"International Application No. PCT/US 09/00773, International Search Report mailed Jul. 1, 2009", 2 pgs.

"International Application No. PCT/US 09/00773, Written Opinion mailed Jul. 1, 2009", 8 pgs.

"International Application No. PCT/US08/08669, International Search Report mailed Oct. 9, 2008", 3 pgs.

"International Application No. PCT/US08/08669, Written Opinion mailed Oct. 9, 2008", 8 pgs.

"International Application No. PCT/US2008/001746, International Search Report mailed May 20, 2008", 2 pgs.

"International Application No. PCT/US2008/001746, Written Opinion mailed May 2008", 6 pgs.

"International Application No. PCT/US2008/001752, International Search Report mailed May 22, 2008", 4 pgs.

"International Application No. PCT/US2008/001752, Written Opinion mailed May 22, 2008", 11 pgs.

"International Application No. PCT/US2008/008076, International Search Report mailed Mar. 3, 2009", 5 pgs.

"International Application No. PCT/US2008/008076, Written Opinion mailed Mar. 3, 2009", 5 pgs.

"International Application No. PCT/US2009/000770, International Search Report mailed Apr. 7, 2009", 2 pgs.

"International Application No. PCT/US2009/000770, Written Opinion mailed Apr. 7, 2009", 9 pgs.

"Poniard Pharmaceuticals", *United States Securities and Exchange Commission—Form10-Q*, For the .quarterly period ended Jun. 30, 2006, 1-74.

"Treatment of First Patient With Picoplatin in Phase ½ Front-Line Prostate Cancer Trial", Retrieved from *Medical News Today*, [online]. Retrieved from the Internet: <URL: http://www.medicalnewstoday.com/articles/44331.php>, (Jun. 1, 2006), 3 pgs.

"Vietnamese Application Serial No. 1-2009-01903, Office Action mailed Nov. 30, 2009", (w/ English Translation), 2 pgs.

Abrams, M. J., et al., "A Convenient Preparation of the Amminetrichloroplatinate(II) Anion", *Inorganica Chimica Acta*, 131, (1987), 3-4.

Akaza, H., et al., "[Platinum compounds in cancer therapy-past, present, and future]", (w/ English Summary), *Gan to Kagaku Ryoho.*, 28(5), (May 2001), 625-635.

Ando, Y., et al., "Potent and Non-Specific Inhibition of Cytochrome P450 by JM216, a New Oral Platinum Agent", (Abstract Only), *British Journal of Cancer*, 78(9), (1998), 1 pg.

Anthoney, D. A, et al., "ZD0473 combined with paclitaxel in refractory solid malignancies: A phase 1 dose-escalation study", (Poster#355), *Clin. Cancer Res.*, 6(Supp), (Nov. 2000), p. 4537s.

Battle, A. R., et al., "Platinum(IV) Analogues of AMD473 (cis-[PtCl$_2$(NH$_3$)(2-picoline)]):Preparative, Structural, and Electrochemical Studies", *Inorganic Chemistry*, 45, (2006), 6317-6322.

Bayes, M., et al., "Gateways to Clinical Trials", *Methods Find Exp Clin Pharmacol.*, 29(8), (Oct. 2007), 547-583.

Bayes, M., et al., "Gateways to Clinical Trials—Jul./Aug. 2003", *Methods Find Exp Clin. Pharmacol*, 25(6), (2003), 483-506.

Bayes, M., et al., "Gateways to Clinical Trials—Mar. 2004" *Methods Find Exp Clin Pharmacol*, 26(2), (2004), 129-161.

Bayes, M., et al., "Gateways to Clinical Trials—Nov. 2004", *Methods Find Exp Clin Pharmacol.*, 26(9), (2004), 723-753.

Bayes, M., et al., "Gateways to Clinical Trials.", *Methods Find Exp Clin Pharmacol.*, 29(10), (Dec. 2007), 697-735.

Beale, P., et al., "A Phase I Clinical Pharmacological Study of cis-diamminedichloro(2-methylpyridine) Platinum II (AMD473)", *British Journal of Cancer*, 88(7), (2003), 1128-1134.

Bentsion, D, et al., "A Phase 2 Study of Picoplatin as Second-line Therapy for Patients with Small Cell Lung Cancer (SCLC) Who Have Resistant or Refractory Disease or Have Releapsed Within 180 Days of Completing First-Line, Platinum-Containing Chemotherapy.", (Poster #7722), *ASCO Annual Meeting*, Chicago, Jun. 1-5, 2007, A Phase 2 Study of Picoplatin, (Jun. 2007), 1 pg.

Bentzion, D., et al., "A phase II study of picoplatin (pico) as second-line therapy for patients (pts) with small cell lung cancer (SClC) who have resistant or refractory disease or have relapsed within 180 days of completing first-line, platinum (plat)-containing chemotherapy.", (Abstract 7722), *Journal of Clinical Oncology, 2007 ASCO Annual Meeting Proceedings Part I*, vol. 25, No. 18S (June 20 Supplement), (2007), 2 pgs.

Bonomi, P., et al., "Phase II Trial to Assess the Activity of ZD0473 in Patients With Small-Cell Lung Cancer Who Have Failed One Prior Platinum-Based Chemotherapy Regimen", (Abstract No. 1284), *Proc. Am. Soc. Clin. Oncol.*, 20, (2001), 2 pgs.

Boulikas, T., et al., "Cisplatin and Platinum Drugs at the Molecular Level (Review)", *Oncology Reports*, 10(6), (2003), 1663-1682.

Braddock, P D, et al., "Structure and Activity Relationships of Platinum Complexes with Anti-tumor Activity.", *Chem.-Biol. Interactions*, 11, (1975), 145-161.

Bratzler, R. L., et al., "Immunostimulatory Nucleic Acids and Cancer Medicament Combination Therapy for the Treatment of Cancer", Provisional U.S. Appl. No. 60/187,214, filed Mar. 3, 2000, 90 pgs.

Breitz, H., et al., "Phase I study of picoplatin and docetaxel (with prednisone) in subjects with chemotherapy-naïve metastatic hormone refractory prostate cancer (HRPC)", (Abstract No: 282), *2007 Prostate Cancer Symposium, American Society of Clinical Oncology*, (2007), 2 pgs.

Cascinu, S., et al., "Recombinant Human Erythropoietin Treatment in Cisplatin-Associated Anemia: A Randomized, Double-Blind Trial With Placebo", *J. Clin. Oncol*; vol. 12(5), (1994), 1058-1062.

Chen, Y., et al., "A New Platinum Anticancer Drug Forms a Highly Stereoselective Adduct with Duplex DNA", *Angewandte Chemie International Edition*, 38(13/14), (1999), 2060-2063.

Chen, Y., et al., "Stereospecific and kinetic control over the hydrolysis of a sterically hindered platinum picoline anticancer complex", *Chem Eur J*, 4(4):672-676, 1998., 672-676.

Cheng, H., et al., "Synthesis, Characterisation, Activities, Cell Uptake and DNA Binding of a Trinuclear Complex: [{trans-PtCl(NH$_3$)}$_2$μ-{trans-Pd(NH$_3$) (2-hydroxypyridine)-(H$_2$N(CH$_2$)$_6$NH$_2$)$_2$]Cl$_4$", *European Journal of Medicinal Chemistry*, 41, (2006), 896-903.

Cheng, H., et al., "Synthesis, Characterization, Activities, Cell Uptake and DNA Binding of a Trinuclear Complex: [{trans-PtCl(NH$_3$)}$_2$μ-{trans-Pd(NH$_3$)(2-hydroxypyridine)-(H$_2$N(CH$_2$)$_6$NH$_2$)$_2$]Cl$_4$", *European Journal of Medicinal Chemistry*, 40, (2005), 772-781.

Chesne, C., et al., "Synthesis and biological studies of aminoestradiol-platinum (II) conjugates", *Eur. J. Med. Chem.—Chim. Ther.*, 21(4), (321-327), 1986.

Cosaert, J., et al., "Platinum Drugs in the Treatment of Non-Small Cell Lung Cancer (Review)", *British Journal of Cancer*, 87(8), (2002), 825-833.

Cubells, M. P, et al., "Stability of cisplatin in sodium chloride 0.9% intravenous solution related to the container's material", *Pharmacy World and Science* vol. 15(1), (1993), 34-36.

Danzeisen, O., et al., "Molekulare gemischtvalente Platin-Iod-Amin-Komplexe: Das dreikernige Pt$_3$I$_8$(NHEt$_3$)$_2$ mit kantenverknüpften planaren und oktaedrischen Baugruppen", *Zeitschrift für anorganische und allgemeine Chemie*, 624(5), (May 1998), 763-768.

Daud, A., et al., "New Drugs in Gynecologic Cancer", *Current Treatment Options in Oncology*, 1, (2001), 119-128.

Davies, A. M., et al., "Treatment of Recurrent Small Cell Lung Cancer", *Hematology/Oncology Clinics of North America*, 18, (2004), 387-416.

Davies, M. S., et al., "Structure, Stability, and Interconversion Barriers of the Rotamers of cis-[Pt$^{II}$Cl$_2$(quinoline)2] and cis-[Pt$^I$Icl$_2$(3-bromoquinoline)(quinoline)] from X-ray Crystallography, NMR Spectroscopy and Molecular Mechanics Evidence", *Inorganic Chemistry*, 40(13), (2001), 3048-3054.

De Graaff, M., et al., "In vitro Antagonistic Cytotoxic Interactions Between Platinum Drugs and Taxanes on Bone Marrow Progenitor Cell CFU-GM", *Anti-Cancer Drugs*, 10, (1999), 213-218.

De Gramont, A., et al., "Leucovorin and Fluorouracil With or Without Oxaliplatin as First-Line Treatment in Advanced Colorectal Cancer", *Journal of Clinical Oncology*, 18(16), (2000), 2938-2947.

De Jager, R. L., et al., "FOLPI (picoplatin/5-fluorouracil/leucovorin) vs modified FOLFOX-6 as a neuropathy-sparing 1st-line therapy for colorectal cancer", *AACR-NCI-EORTIC Molecular Targets and Cancer Therapeutics International Conference*, Boston, MA; Nov. 15-19, 2009, 2 pgs.

De Jager, R. L., et al., "Phase II study of picoplatin with docetaxel and prednisone in first-line treatment of castration-resistant prostate cancer". *American Society of Clinical Oncology (ASCO) 2010, Genitourinary Cancers Symposium*, San Francisco, CA (Mar. 5-7, 2010), 1 pg.

De Jager, R. L., et al., "Phase II study of picoflatin with docetaxel and prednisone in first-line treatment of castration-resistant prostate cancer". (Abstract Only), *American Society of Clinical Oncology (ASCO) 2010 Genitourinary Cancers Symposium*, (San Francisco, California, Mar. 5-7, 2010), 1 pg.

De Jager, R. L., et al., "Randomized phase 2 study of picoplatin in combination with 5-fluorouracil and leucovorin (FOLPI) as a neuropathy-sparing alternative to mFOLFOX-6 as first-line therapy for colorectal cancer.", *AACR-NCI-EORTC International Conference: Molecular Targets and Cancer Therapeutics*, (Poster Presentation) (Boston, Massachusetts, Nov. 15-19, 2009), 1 pg.

De Jager, R. L. at al., "Randomized Phase 2 Study of Picoplatin in Cobination with 5-Fluorouricil and Leucovorin (FOLIP) as a Neuropathy-sparing Alternative to mFOLFOX-6 as First-line Therapy and Colorectal Cancer (CRC)", *ASCO 2010 Gastrointestinal Cancers Symposium: Science and Multidisplinary Management of GI Malignancies*, (Orlando, FL Jan. 22-24, 2010), 1 pg.

Dhara, S C, "A Rapid Method for the Synthesis of cis-[Pt(NH$_3$)2Cl$_2$]", *Indian J. Chem.*, 8, (1970), 194-194.

Dizon, D. S., et al., "A comparison of gene expression analyses in SKOV-3 and wild-type and resistant ovarian carcinoma cells following treatment with cisplatin and a non-cross resistant platinum analogue, ZD-0473", (Abstract #2276), *Proceedings of the AACR*, 42, (2001), p. 423

Dizon, D. S., et al., "Phase I Study of ZD0473 and Liposomal Doxorubicin in Advanced Refractory Solid Tumor Malignancies", (Abstract No. 273), *European Journal of Cancer*, 37 (Suppl. 6), (2001), p. S77

Dolan, S., et al., "Gene expression profiles associated with platinum drug sensitivity and resistance in human ovarian cancer cells", (Abstract #2275), *Proceedings of the AACR*, 42, (2001), 423-424.

Douillard, J., et al., "Phase I Trial of ZD0473 in Combination With Vinorelbine for Patients With Advanced Cancer",(Abstract No. 274), *European Journal of Cancer*, 37 (Suppl. 6), (2001), p. S77

Douillard, J.-Y., et al., "ZD0473 Combined With Other Chemotherapeutic Agents for the Treatment of Solid Malignancies", *European Journal of Cancer*, 38 (Suppl. 8), (2002), S25-S31.

Dupont, J., et al., "*Cis* and *trans* nucleophilic additions on C≡C bonds assisted by Pt(II) complexes. X ray crystal structure of trans-[Pt[-cis-(o-NC$_5$H$_4$)CH=C(Ph)(Net$_2$)Cl$_2$ (HNEt$_2$),", *Polyhedron*, 13(17), (1994), 2583-2587.

Earhart, R. H., et al., "FOLPI (picoplatin/5-fluorouracil/leucovorin) vs modified FOLFOX-6 as a neuropathy-sparing 1$^{st}$-line therapy for colorectal cancer (CRC)", (Abstract Only), *AACR-NCI-EORTC International Conference: Molecular Targets and Cancer Therapeutics*,B49) (Nov. 15-19, 2009, Boston, MA), 1 pg.

Earhart, R. H., et al., "QTc study of picoplatin with emphasis on pharmacodynamics of cardiac repolarization", (Abstract Only), *AACR-NCI-EORTC International Conference: Molecular Targets and Cancer Therapeutics*, (Nov. 15, 2009), 2 pgs.

Earhart, R. H., et al., "QTc study of picoplatin with emphasis on pharmacodynamics of cardiac repolarization", *AACR-NCI-EORTC International Conference: Molecular Targets and Cancer Therapeutics*, (Poster Presentation), (Boston, Massachusetts, Nov. 15-19, 2009), 1 pg.

Eckardt, John R, "Picoplatin in Relapsed Small-cell Lung Cancer", *Lung Cnacer* 78-80, 2007, 78-80.

Emmanouilides, C., et al., "Front-line Bevacizumab in combination with Oxaliplatin, Leucorvin and 5-Fluorouracil (FOLFOX) in patients with metastatic colorectal cancer: a multicenter phase II study", *BMC Cancer*, vol. 7 (91), (May 2007), 1-7 pgs.

Flaherty, K. T., et al., "A Phase I, Dose Escalation Trial of ZD0473, a Novel Platinum Analogue, in Combination With Gemcitabine", *Cancer Chemother. Pharmacol.*, 53(5), (2004), 404-408.

Gatzemeier, U., et al., "A Phase I Dose-Escalation Study of ZD0473 Combined With Paclitaxel in Refractory Solid Malignancies", (Abstract 264), *Eur. J. Cancer*, 37 (Suppl. 6), (2001), p. S74.

Gelmon, K. A., et al., "A Phase I Study of AMD473 and Docetaxel Given Once Every 3 Weeks in Patients With Advanced Refractory Cancer: A National Cancer Institute of Canada-Clinical Trials Group Trial, IND 131", *Annals of Oncology*, 15(7), (2004), 1115-1122.

Gelmon, K. A., et al., "A Phase II Study of ZD0473 Given as a Short Infusion Every 3 Weeks to Patients With Advanced or Metastic Breast Cancer: A National Cancer Institute of Canada Clinical Trials Group trial, IND 129", *Annals of Oncology*, 14(4), (2003), 543-548.

Giaccone, G., et al., "Phase II Trial of ZD0473 as Second-Line Therapy in Mesothelioma", *European Journal of Cancer*, 38 (Suppl. 8), (2002), S19-S24.

Giandomenico, C. M., et al., "Carboxylation of Kinetically Inert Platinum(IV) Hydroxy Complexes. An I Into Orally Active Platinum(IV) Antitumor Agents", *Inorg. Chem.*, 34, (1995), 1015-1021.

Gladkov, O., et al., "Phase 1 study of picoplatin (pico) in combination with 5-fluorouracil (FU) and leucovorin (LV) as initial therapy in subjects with metastatic colorectal cancer (CRC)", (Abstract 14510), *Journal of Clinical Oncology, 2007 ASCO Annual Meeting Proceedings Part I*. vol. 25 No. 18S (Supplement), , (2007), 1 pg.

Gladkov, O., et al., "Phase I study of picoplatin (pico) in combination with 5-fluorourcil (FU) and leucovorin (LV) as initial therapy in subjects with metastatic colorectal cancer (CRC)", (Abstract Only), *Journal of Clinical Oncology, 2007 ASCO Annual Meeting Proceedings (Post-Meeting Edition)*, 25(185), (2007), 2 pgs.

Glisson, B. S., "Recurrent Small Cell Lung Cancer: Update", *Seminars in Oncology*, 30(1), (2003), 72-78.

Goldberg, R. M, et al., "A Randomized Controlled Trial of Fluorouracil Plus Leucovorin, Irinotecan, and Oxaliplatin Combinations in Patients With Previously Untreated Metastatic Colorectal Cancer", *Journal of Clinical Oncology*, 22(1), (2004), 23-30.

Gore, M. E., et al., "A Phase II Trial of ZD0473 in Platinum-Pretreated Ovarian Cancer", *European Journal of Cancer*, 38, (2002), 2416-2420.

Gore, M. E., et al., "Results of ZD0473 in Platinum-Pretreated Ovarian Cancer: Analysis According to Platinum Free Interval", *European Journal of Cancer*, 38 (Suppl. 8), (2002), S7-S12.

Gore, M., et al., "ZD0473 Phase II Monotherapy Trial in Second-Line Ovarian Cancer", (Abstract 2501), *Proc Am Soc Clin Oncol 20*, 2001 ASCO Annual Meeting, (2001), 2 pgs.

Gore, M. E, et al., "ZD0473 phase II monotherapy trial in second-line ovarian cancer", (Abstract 881), *Proc Am Soc Clin Oncol*, 21, (2002), 2 pgs.

Hartmann, J. T., et al., "Toxicity of Platinum Compounds (Review)", *Expert Opin. Pharmacother.*, 4(6), (2003), 889-901.

Hausner, P. F., et al., "The Growth Inhibitory Effect of ZD0473 a Novel Platinum Compound is Not Influenced by Mismatch Repair Proficiency", (Abstract #4362 and Poster #4362) *Proceedings of the American Association for Cancer Research*, 42, (Mar. 2001), p. 813.

Hay, M. P., "ZD-0473 AstraZeneca", *Current Opinion in Investigational Drugs*, 1(2), (2000), 263-266.

Hiorns, L. R., et al., "A Molecular Cytogenetic Approach to Studying Platinum Resistance", *Journal of Inorganic Biochemistry*, 77, (1999), 95-104.

Hoctin-Boes, G., et al., "Safety Profile of ZD0473 in Phase II Trials of Patients With Advanced Cancers", (Abstract 1372), *Proceedings, 2001 ASCO Annual Meeting*, (2001), 2 pgs.

Hoctin-Boes, G., et al., "Safety Profile of ZD0473 in Phase II Trials of Patients With Advanced Cancers", (Poster P243),*British Journal of Cancer*, (2001), p. 95.

Holford, J., et al., "Chemical, Biochemical and Pharmacological Activity of the Novel Sterically Hindered Platinum Co-ordination Complex, cis[amminedichloro(2-methylpyridine)] platinum(II) (AMD473)", *Anti-Cancer Drug Design*, 13, (1998), 1-18.

Holford, J., et al., "In vitro Circumvention of Cisplatin Resistance by the Novel Sterically Hindered Platinum Complex AMD473", *British Journal of Cancer*, 77(3), (1998), 366-373.

Holford, J., et al., "In vitro examination of JM473, a novel sterically hindered platinum (II) complex", (Abstract 122), *Annals of Oncology*, (Supplement 1), 37, 9$^{th}$ NCI-EORTC Symposium on New Drugs in Cancer Therapy, (1996), p. 37.

Holford, J., et al., "Mechanisms of Drug Resistance to the Platinum Complex ZD0473 in Ovarian Cancer Cell Lines", *European Journal of Cancer*, 36, (2000), 1984-1990.

Hollis, L. S., et al., "Chemical and Biological Properties of a New Series of cis-Diammineplatinum(II) Antitumor Agents Containing Three Nitrogen Donors: $cis[Pt(NH_3)_2(N\ donor)Cl^{+}]$", *J. Med. Chem*, 32, (1989), 128-136.

Huisman, C., et al., "Second-Line Chemotherapy and its Evaluation in Small Cell Lung Cancer", *Cancer Treatment Reviews*, 25, (1999), 199-206.

Huq, F., et al., "Synthesis, Characterisation, Activities, Cell Uptake and DNA Binding of $[\{trans\text{-}PtCl(NH_3)_2\}\ \{\mu\text{-}(H_2N(CH_2)_6NH_2)\}\ \{trans\text{-}PdCl(NH_3)_2\}](NO_3)Cl$", *European Journal of Medicinal Chemistry*, 39, (2004), 947-958.

Ikeda, J., et al., "Phase I study of amrubicin hydrochloride and cisplatin in patients previously treated for advanced non-small cell lung cancer.", *Jpn J Clin Oncol.*, 36(1), (Jan. 2006), 12-16.

Inoue, A., et al., "A phase I study of amrubicin combined with carboplatin for elderly patients with small-cell lung cancer", *J Thorac Oncol.*, 1(6), (Jul. 2006), 551-555.

Ivanova, M. I., *2h Neorq Khim*, 2 (Russian), (1957), 1317-1323.

Ivanova, M. I, "Complex compounds of bivalent platinum with isomeric alpha and beta picolines I. The alpha and beta picoline compounds of platinum CA 52:20255", *Chemical Abstracts*, 52, (1958), p. 3587.

Johnson, B. E, et al., "Small cell lung cancer clinical practice guidelines in oncology", *J Natl Compr Canc Netw.*, 4(6), (Jul. 2006), 602-22.

Judson, I., et al., "New Developments and Approaches in the Platinum Area", *Drugs*, 59 (Supp. 4), (2000), 29-36.

Kanzawa, F, et al., "In vitro effects of the combination of ZD-0473 and gemcitabine in human lung cancer cells", (Abstract Only), 12$^{th}$ *NCI-EORTC-AACR Conference*, Miami FL, (2001),1 pg.

Kanzawa, F, et al., "In vitro effects of the combination of ZD0473 and gemcitabine in human lung cancer cells", (Poster #721), 12$^{th}$ *AACR-NCI-EORTC International Conference*, (Miama, FL, Oct. 29-Nov. 2, 2001), (2001), 1 pg.

Kanzawa, F., et al., "In vitro Effects of Combinations of cis-amminedichloro (2-methylpyridine) Platinum (II) (ZD0473) With Other Novel Anticancer Drugs on the Growth of SBC-3, a Human Small Cell Lung Cancer Cell Line", *Lung Cancer*, 40, (2003), 325-332.

Karlin, D., et al., "A Phase 2 study of Picoplatin monotherapy for patients with small cell lung cancer (SCLC) who have resistant or refractory disease or have relapsed within 180 days of completing first-line, Platinum containing chemotherapy", (No. PD6-1-1) , *Journal of Thoracic Oncology*, 2(8)(Supp. 4), (2007), pp. S424-S425.

Kauffman, G. B., et al., "cis- and trans-Dichlorodiammine-Platinum(II)", *Inorg. Synth.* 7, (1963), 239-245.

Kawamura-Akiyama, Y., et al., "Non-Cross Resistance of ZD0473 in Acquired Cisplatin-Resistance Lung Cancer Cell Lines", *Lung Cancer*, 38, (2002), 43-50.

Kelland, L. R., et al., "AMD473—JM-473, ZD-0473", *Drugs of the Future*, 23(10), (1998), 1062-1065.

Kelland, L., "Broadening the Clinical Use of Platinum Drug-Based Chemotherapy With New Analogues: Satraplatin and Picoplatin", *Expert. Opin. Investig. Drugs*, 16(7), (2007), 1009-1021.

Kelland, L. R, et al., "JM473: a novel sterically hindered platinum (II) complex showing non cross-resistance properties to cisplatin", (Abstract 2748), *Proc Am Assoc Cancer Res*, 37, 87$^{th}$ Annual Meeting. (1996), p. 403.

Kelland, L. R., "Meeting Report on 8$^{th}$ International Symposium on Platinum and Other Metal Coordination Compounds in Cancer Chemotherapy", *Journal of Inorganic Biochemistry*, 77(1-2), (1999), 121-124.

Kelland, L. R., et al., "Mini-Review: Discovery and Development of Platinum Complexes Designed to Circumvent Cisplatin Resistance", *Journal of Inorganic Biochemistry*, 77, (1999), 111-115.

Kelland, L., et al., "Preclinical and Clinical Overview of the Novel Platinum Complex, ZD0473 (cis-amminedichloro[2-methylpyridine] Platinum[II])", (Abstract 227), *Lung Cancer,*29 (Suppl.I), (2000), p. 70.

Kelland, L. R., "Preclinical Perspectives on Platinum Resistance", *Drugs*, 59 (Suppl. 4), (2000), 1-8.

Kelland, L., "The Resurgence of Platinum-Based Cancer Chemotherapy", *Nature Reviews*, 7, (2007), 573-584.

Koizumi, F., et al., "Effect of ZD0473 on specific gene transcript in a human lung cancer cell line and its cisplatin subline", *International Congress of Chemotherapy*, Amsterdam, (Jul. 2001), 1 pg.

Kong, P.-C., et al., "Reactions of $K_2PtCl_4$ With Pyridine Derivatives in Dimethylformamide and Synthesis of Potassium Trichloro(pyridine)platinum(II)", *Canadian Journal of Chemistry*, 56, (1978), 441-445.

Kostova, I., "Platinum Complexes as Anticancer Agents", *Recent Patents on Anti-Cancer Drug Discovery*, 2006, 1, 1-22., (2006), 1-22.

Lahoz De Juan, C., et al., "Response to Chemotherapy (CT) and Outcome in Patients With Relapsed of Refractory Ovarian (RROC)", (Abstract No. 338), *Annals of Oncology*, (vol. 9, Suppl. 4), (1998), p. 70.

Lansiaux, A., et al., "Perspectives sur la pharmacopee de l'oncologue <Perspectives on the Oncologist Pharmacopoeia>", *Bull. Cancer*, 90(1), (2003), 25-30.

Latorre, A., et al., "Epithelial Ovarian Cancer: Second and Third Line Chemotherapy (Review)", *International Journal of Oncology*, 20(1), (2002), 179-186.

Leyland-Jones, B., et al., "Genomic Imbalances Associated With Acquired Resistance to Platinum Analogues", *American Journal of Pathology*, 155(1), (1999), 77-84.

Lin, X., et al., "The Copper Transporter CTR1 Regulates Cisplatin Uptake in *Saccharomyces cerevisiae*", *Molecular Pharmacology*, 62(5), (2002), 1154-1159.

Lipp, H.-P., et al., "Platinverbindungen: Metabolismus, Toxizität and Supportive Strategien", *Praxis*, 94, (2005), 187-198.

Loprevite. M., et al., "Pre-clinical evaluation of new antineoplastic agents in NSCLC cell lines: evidence of histological subtype-dependent cytotoxicity", *Int J Oncol.*, 15(4) (Oct. 1999), 787-792.

Ma, Y., et al., "Synthesis, structure, and reactivity of monofunctional platinum(II) and palladium (II) complexes containing the sterically hindered ligand 6-methylpyridin-2-yl)acetate", *Journal of Inorganic Biochemistry*, 99, (2005), 2013-2023., (2005), 2013-2023.

Maindrault-Goebel, F., et al., "Evaluation of oxaliplatin dose intensity in bimonthly leucovorin and 48-hour 5-fluorouracil continuous infusion regimens (FOLFOX) in pretreated metastatic colorectal cancer. Oncology Multidisciplinary Research Group (GERCOR).", *Ann Oncol.*, 11(11), (Nov. 2000), 1477-1483.

Markman, M., et al., "Evidence That a "Treatment-Free Interval of Less Than 6 Months" Does not Equate With Clinically Defined Platinum Resistance in Ovarian Cancer or Primary Peritoneal Carcinoma", *J. Cancer Res. Clin. Oncol.*, 124, (1998), 326-328.

Markman, M., et al., "Second-Line Platinum Therapy in Patients With Ovarian Cancer Previously Treated With Cisplatin", *Journal of Clinical Oncology*, 9(3), (1991), 389-393.

McGowan, G., et al., "Contrasting Chemistry of *cis*- and *trans*-Platinum(II) Diamine Anticancer Compounds: Hydrolysis Studies of Picoline Complexes", *Inorganic Chemistry*, 44, (2005), 7459-7467

McGowan, G., et al., "G-G Base-Pairing in Nucleobase Adducts of the Anticancer Drug *cis*-[PtCl$_2$(NH$_3$)(2-picoline)] and Its *trans* Isomer", *Chemistry—A European Journal*, 11, (2005), 4396-4404.

McGuire, W. P., et al., "Chemotherapy of Advanced Ovarian Cancer", *Seminars in Oncology*, 25(3), (1998), 340-348.

Medina-Gundrum, L., et al., "AMD473 (ZD473) Exhibits Marked in vitro Anticancer Activity in Human Tumor Specimens Taken Directly From Patients", *Anti-Cancer Drugs*, 14, (2003), 275-280.

Miner, C. B., et al., "Characterisation of a Polyclonal Antibody Raised to DNA Adducts of AMD473", (Abstract P10), *Br. J. Cancer*, 75(Suppl 1), (1997), p. 21.

Munk, V. P., et al., "Investigations Into the Interactions Between DNA and Conformationally Constrained Pyridylamineplatinum(II) Analogues of AMD473", *Inorganic Chemistry*, 42(11), (2003), 3582-3590.

Murakami, H., et al., "ZD0473 Pharmacokinetics in Japanese Patients: A Phase I Dose-Escalation Study", *European Journal of Cancer*, 38 (Suppl. 8), (2002), S1-S5.

Natile, G., et al., "Current Status of *trans*-platinum Compounds in Cancer Therapy", *Coordination Chemistry Reviews*, 216-217, (2001), 383-410.

Negoro, S., et al., "Recent progress in chemotherapy for advanced lung cancer", *Gan to Kagaku Ryoho*; vol. 22(4), (1995), 451-460.

O'Dwyer, P. J., et al., "Phase I Trial of the Novel Platinum Analog ZD0473 in Combination with Gemcitabine (GEM) for Patients with Advanced Cancers", (Abstract #1354), *Proc Am Soc Clin Oncol*, 20, (2001), p. 339a.

O'Dwyer, P., et al., "Phase I Trial of the Novel Platinum Analog ZD0473 in Combination With Gemcitabine in Patients With Advanced Cancer", (Abstract No. 252), *European Journal of Cancer*, 37 (Suppl. 6), (2001), p. S71.

O'Dwyer, P. J, et al., "Phase I Trial of the Novel Platinum Analogue ZD0473 in Combination with Gemcitabine (GEM) for Patients with Advanced Cancers", (Abstract No. 1354), *Proc Am Soc Clin Oncol*, 20, 2001 ASCO Annual Meeting, (2001), 2 pgs.

Oe, T., et al., "A Liquid Chromatography/Tandem Mass Spectrometry Assay for *Cis*-Amminedichloro(2-Methylpyridine) Platinum(II) (ZD0473) in Human Plasma Ultrafiltrate", *European Conference of Clinical Oncology*, (London, United Kingdom), (Oct. 2001), 2 pgs..

Oe, T., et al., "A Liquid Chromatography/Tandem Mass Spectrometry Assay for Cis-Amminedichloro(2-Methylpyridine)Platinum(II) (ZD0473) in Human Plasma Ultrafiltrate", (Abstract No. 243), *European Conference of Clinical Oncology (ECCO 11)*, Oct. 21-25, 2011, Lisbon, (2001), 1 pg.

Oe, T., et al., "A Validated Liquid Chromatography/Tandem Mass Spectrometry Assay for cis-Amminedichloro(2-methylpyridine)platinum(II) in Human Plasma Ultrafiltrate", *Analytical Chemistry*, 74(3), (2002), 591-599.

Oe, T., et al., "Analysis of Cis-Amminedichloro(2-Methylpyridine) Platinum(II) (ZD0473) in Human Urine", (Abstract No. 245), *European Conference of Clinical Oncology (ECCO 11)*, (Oct. 21-25, 2001, Lisbon), (2001), 1 pg.

Oe, T., et al., "Analysis of *Cis*-Amminedichloro(2-Methylpyridine) Platinum(II) (ZD0473) in Human Urine", *European Conference of Clinical Oncology*, (London, United Kingdom), (Oct. 2001), 2 pgs.

Oe, T., et al., "Determination of the Platinum Drug cis-amminedichloro(2-methylpyridine)Platinium(II) in Human Urine by Liquid Chromatography-Tandem Mass Spectrometry", *Journal of Chromatography B*, 792, (2003), 217-227.

One, Y., et al., "Phase I-II study of amrubicin and cisplatin in previously untreated patients with extensive-stage small-cell lung cancer. ", *Ann Oncol.*, 16(3), (Mar. 2005), 430-6.

Osborne, R., "Magic Bullet Still Missing for Lung Cancer Sufferers", *BioWorldl Financial Watch*, vol. 12, No. 38, (Sep. 19, 2005), 2 pgs.

Park, H. S., et al., "Randomized Trial of Docetaxel Plus Cipslatin (DC) Versus Etoposide Plus Cisplatin (EC) in Locally Advanced, Recurrent, or Metastatic Non-Small Cell Lung Cancer (NSCLC)", (Poster 799), *Proc. Am. Soc. Clin. Oncol.*, 22, (2003), p. S240.

Parker, S. L., "Cancer Statistics, (1997)", *CA—A Cancer Journal for Clinicians*, 47(1), (1997), 5-27.

Perez, R. P., "Cellular and Molecular Determinants of Cisplatin Resistance", *European Journal of Cancer*, 34(10), (1998), 1535-1542.

Pestell, K. E., et al., "Characterisation of the P53 Status, BCL-2 Expression and Radiation and Platinum Drug Sensitivity of a Panel of Human Ovarian Cancer Cell Lines", *Int. J. Cancer*, 77, (1998), 913-918.

Pestell, K. E., et al., "Effect of p53 Status on Sensitivity to Platinum Complexes in a Human Ovarian Cancer Cell Line", *Molecular Pharmacology*, 57, (1999), 503-511.

Pfeffer, M, et al., "Etude spectroscopique de composes carres pands du Pt(II) et du Pd(II) avec des pyridines substituees I. Vibrations des coordiats.", *Spectrochemica Acta*, 30A, in French, (1974), 331-340.

Phillips, A, et al., "Interspecies Allometric Scaling of Picoplatin in Mouse, Rat, Dog and Human", (Abstract Only), *AACR-NCI-EORTC International Conference: Molecular Targets and Cancer Therapieutics*, (Nov. 15, 2009), 1 pg.

Piccart, M. J., et al., "Current and Future Potential Roles of the Platinum Drugs in the Treatment of Ovarian Cancer", *Annals of Oncology*, 12, (2001), 1195-1203.

Plasencia, C., et al., "Antiproliferative Effects of ZD0473 (AMD473) in Combination With 5-Fluorouracil or SN38 in Human Colorectal Cancer Cell Lines", *Investigational New Drugs*, 22(4), (2004), 399-409.

Plasencia, C., et al., "Preclinical Synergy of ZD0473 in Combination With 5FU and SN38 in Sensitive and 5FU-Resistant Colon Cancer Cell Lines", (Abstract No. 5408), *Proceedings of the 93$^{rd}$ Annual Meeting of the American Association for Cancer Research*, vol. 43, (2002), p. 1091.

Pointeau, P., et al., "Synthesis and Structure of Platinum(II) (aminophenol (pyridine) Complexes,", *Eur. J. Med. Chem.—Chem Ther.* 1985, 20(4), 327-32., [CA: 103:226258x]., (1985), 327-332.

Poniard Pharmaceuticals, Inc., "Poniard Pharmaceuticals Announces 2010 Goals for Picoplatin", Press Release, (Jan. 7, 2010), 3 pgs.

Poniard Pharmaceuticals, Inc., "Poniard Pharmaceuticals Announces Phase 2 Trial of Picoplatin in Metastatic Colorectal", (Jan. 24, 2010), 2 pgs.

Poniard Pharmaceuticals, Inc., "Poniard Pharmaceuticals Announces Updated Positive Clinical Data from Phase 2 Trial of Picoplatin in Colorectal Cancer and New Phase 1 Cardiac Safety Trial Results", (Nov. 17, 2009), 2 pgs.

Poniard Pharmaceuticals, Inc., "Poniard Pharmaceuticals Announces Pivotal Phase 3 SPEAR Trial Evaluating Picoplatin in Small Cell Lung Cancer Reaches 320$^{th}$ Event Target", *Press Release*, (Sep. 15, 2009), 2 pgs.
Poniard Pharmaceuticals, Inc., "Poniard Pharmaceuticals Announces Pivotal Phase 3 SPEAR Trial of Picoplatin in Small Cell Lung Cancer Did Not Meet Primary Endpoint", *Press Release*, (Nov. 16, 2009), 2 pgs.
Poniard Pharmaceuticals, Inc., "Poniard Pharmaceuticals Announces Positive Cardiac Safety Data From Picoplatin Phase 1 Trial Supporting NDA Filing", *Press Release*, (Jul. 21, 2009), 2 pgs.
Poniard Pharmaceuticals, Inc., "Poniard Pharmaceuticals Announces Positive Efficacy and Safety Data From Phase 2 Clinical Trial of Picoplatin in Men With Metastatic Prostate Cancer", *Press Release*, (May 28, 2009), 3 pgs.
Poniard Pharmaceuticals, Inc., "Poniard Pharmaceuticals Announces Progression-Free Survival Data From Phase 2 Clinical Trial of Picoplatin in Metastatic Colorectal Cancer", *Press Release*, (May 28, 2009), 3 pgs.
Poniard Pharmaceuticals, Inc., "Poniard Pharmaceuticals to Host Conference Call and Webcast at 8:00 a.m. Eastern Time Tomorrow to Discuss Results of Pivotal Phase 3 SPEAR Trial in Small Cell Lung Cancer", *Press Release*, (Nov. 15, 2009), 1 pg.
Poniard Pharmaceuticals, Inc., "Poniard Pharmaceuticals to Present at the 2009 UBS Global Life Sciences Conference", *Press Release*, (Sep. 16, 2009), 1 pg.
Poniard Pharmaceuticals, Inc., "Poniard Pharmaceuticals to Present at the 8$^{th}$ Annual Needham Life Sciences Conference", *Press Release*, (Jun. 5, 2009), 1 pg.
Poniard Pharmaceuticals, Inc., "Poniard Pharmaceuticals to Present at Three Upcoming Investor Conferences in September", *Press Release*, (Sep. 2, 2009), p. 1.
Poniard Pharmaceuticals, Inc., "Poniard Pharmaceuticals to Present at Two Upcoming Investor Conferences in August", *Press Release*, (Jul. 29, 2009), 1 pg.
Poniard Pharmaceuticals, Inc., "Poniard Pharmaceuticals to Present Updated Clinical Data from Phase 2 Trial of Picoplatin in Colorectal Cancer and Final Phase 1 Cardiac Safety Trial Results", *Press Release*, (Nov. 10, 2009), 2 pgs.
Poniard Pharmaceuticals, Inc., "Jerry McMahon Named NeoRx Chairman", *Press Release*, (Jun. 24, 2004), 2 pgs.
Poniard Pharmaceuticals, Inc., "NeoRx Acquires Cancer Compound from AnorMED; Acquisition Broadens Product Pipeline and Complements STR Development Program", *Press Release*, (Apr. 5, 2004), 2 pgs.
Poniard Pharmaceuticals, Inc., "NeoRx Annonces Treatment of First Patient with Picoplatin in Phase 2 Clinical Trial in Small Cell Lung Cancer", *Press Release*, (Jul. 11, 2005), 2 pgs.
Poniard Pharmaceuticals, Inc., "NeoRx Announces Appointment of Distinguished Oncologist Alan B. Glassberg, M.D. to Board of Directors", *Press Release*, (Oct. 25, 2004), 2 pgs.
Poniard Pharmaceuticals, Inc., "NeoRx Announces IND Filing for NX 473 Next Generation Platinum Compound to Treat Small Cell Lung Cancer", *Press Release*, (Oct. 26, 2004), 2 pgs.
Poniard Pharmaceuticals, Inc., "NeoRx Announces Orphan Drug Designation for Picoplatin for Treatment of Small Cell Lung Cancer", *Press Release*, (Nov. 10, 2005), 2 pgs.
Poniard Pharmaceuticals, Inc., "NeoRx Corporation (Poniard Pharmaceuticals) Announces Treatment of First Patient with Picplatin in Phase ½ Front-line Prostate Cancer Trial", *Press Release*, (May 31, 2006), 2 pgs.
Poniard Pharmaceuticals, Inc., "NeoRx Corporation (Poniard Pharmaceuticals) Reports First Quarter Financial Results", *Press Release*, (May 15, 2006), 3 pgs.
Poniard Pharmaceuticals, Inc., "NeoRx Expands Picoplatin Lung Cancer Clinical Trial into Selected Eastern European Countries", *Press Release*, (Apr. 25, 2006), 2 pgs.
Poniard Pharmaceuticals, Inc., "NeoRx Initiates Clinical Trial of Picoplatin in Colorectal Cancer and Announces Name Change to Poniard Pharmaceuticals and Relocation of Corporate Headquarters", *Press Release*, (May 10, 2006), 3 pgs.

Poniard Pharmaceuticals, Inc., "NeoRx Refocusing Resources to Expedite Development of Picoplatin", *Press Release*, (May 6, 2005), 2 pgs.
Poniard Pharmaceuticals, Inc., "NeoRx Reports First Quarter 2004 Results", *Press Release*, (Apr. 23, 2004), 3 pgs.
Poniard Pharmaceuticals, Inc., "NeoRx Reports Fourth Quarter and Full Year Financial Results and Corporate Highlights", *Press Release*, (May 16, 2005), 4 pgs.
Poniard Pharmaceuticals, Inc., "NeoRx Reports Second Quarter 2005 Financial Results", *Press Release*, (Aug. 9, 2005), 3 pgs.
Poniard Pharmaceuticals, Inc., "NeoRx Reports Third Quarter 2004 Financial Results", *Press Release*, (Nov. 4, 2004), 4 pgs.
Poniard Pharmaceuticals, Inc., "NeoRx Reports Third Quarter 2005 Financial Results", *Press Release*, (Nov. 9, 2005), 3 pgs.
Poniard Pharmaceuticals, Inc., "NeoRx Sells Pretarget Intellectual Property; NeoRx Announces Resignation of Vice President, Finance", *Press Release*, (Apr. 5, 2004), 2 pgs.
Poniard Pharmaceuticals, Inc., "NeoRx's NX 473 Next Generation Platinum Compound Dmonstrates Activity in Colorectal Cancer Cells Resistant to Chemotherapeutics", *Press Release*, (Nov. 23, 2004), 2 pgs.
Poniard Pharmaceuticals, Inc., "Poniard Announces Positive Interim Survival Results from Ongoing Phase 2 Trial of Picoplatin for Small Cell Lung Cancer", *Press Release*, (Nov. 6, 2006), 2 pgs.
Poniard Pharmaceuticals, Inc., "Poniard Pharmaceuticals Announces European Commission Grants Orphan Medicinal Product Designation to Picoplatin for Treatment of Small Cell Lung Cancer", *Press Release*, (Oct. 17, 2007), 2 pgs.
Poniard Pharmaceuticals, Inc., "Poniard Pharmaceuticals Announces Initiation of Picoplatin Phase 2 Trial in First-line Treatment of Hormone-Refractory Prostate Cancer in Combination with Docetaxel and Prednisone", *Press Release*, (Jul. 31, 2007), 2 pgs.
Poniard Pharmaceuticals, Inc., "Poniard Pharmaceuticals Announces Picoplatin Abstract Accepted for Publication by ASCO's 2007 Prostate Cancer Symposium", *Press Release*, (Feb. 22, 2007), 2 pgs.
Poniard Pharmaceuticals, Inc., "Poniard Pharmaceuticals Announces Promising Data From Interim Safety Analysis of Phase 1 Combination Trials of Picoplatin in Colorectal and Prostate Cancer", *Press Release*, (Jun. 1, 2007), 3 pgs.
Poniard Pharmaceuticals, Inc., "Poniard Pharmaceuticals Announces Results of Picoplatin Phase 2 Trial that Confirm and Extend Surivial Benefit of Small Cell Lung Cancer", *Press Release*, (Jun. 3, 2007), 3 pgs.
Poniard Pharmaceuticals, Inc., "Poniard Pharmaceuticals Announces Treatment of First Patient in Phase 1 Trial of Oral Formulation of Picoplatin", Press Release, (Apr. 13, 2007), 1 pg.
Poniard Pharmaceuticals, Inc., "Poniard Pharmaceuticals Announces Treatment of First Patient with Picoplatin in Pivotal Phase 3 Small Cell Lung Cancer Trial", *Press Release*, (May 1, 2007), 2 pgs. .
Poniard Pharmaceuticals, Inc., "Poniard Pharmaceuticals Announces Updated Results of Picoplatin Phase 2 Trial Demonstrating Surivial Benefit in Small Cell Lung Cancer Patients", *Press Release*, (Sep. 4, 2007), 3 pgs.
Poniard Pharmaceuticals, Inc., "Poniard Pharmaceuticals Announes Clinical Data from Picoplatin Phase 2 Small Cell Lung Cancer Trial to be Presented at American Society of Clinical Oncology Annual Meeting", *Press Release*, (May 23, 2007), 2 pgs.
Poniard Pharmaceuticals, Inc., "Poniard Pharmaceuticals Completes Enrollment in Picoplatin Phase 2 Small Cell Lung Cancer Clinical Trial", *Press Release*, (Aug. 17, 2006), 2 pgs.
Poniard Pharmaceuticals, Inc., "Poniard Pharmaceuticals Expands Picplatin Agreement to Include Exclusive Worldwide Rights and Improved Financial Terms and Conditions", *Press Release*, (Sep. 19, 2006), 3 pgs.
Poniard Pharmaceuticals, Inc., "Poniard Pharmaceuticals Files Investigational Drug Application for Oral Formulation of Picoplatin", *Press Release*, (Feb. 13, 2007), 2 pgs.
Poniard Pharmaceuticals, Inc., "Poniard Pharmaceuticals Initiates Randomized Phase 2 Trial of Picoplatin for First-line Treatment of Metastatic Colorectal Cancer", *Press Release*, (Nov. 1, 2007), 2 pgs.
Poniard Pharmaceuticals, Inc., "Poniard Pharmaceuticals Provides Year-End Clinical Update at 2007 Lazard Capital Markets Healthcare Conference", *Press Release*, (Nov. 27, 2007), 2 pgs.

Poniard Pharmaceuticals, Inc., "Poniard Pharmaceuticals Receives FDA Fast Track Designation for Picoplatin for Treatment of Small Cell Lung Cancer", *Press Release*, (Sep. 5, 2007), 2 pgs.

Poniard Pharmaceuticals, Inc., "Poniard Pharmaceuticals Receives Special Protocol Assessment for Pivotal Phase 3 Trial of Picoplatin for Small Cell Lung Cancer", *Press Release*, (Jan. 3, 2007), 2 pgs.

Poniard Pharmaceuticals, Inc., "Poniard Pharmaceuticals Reports First Quarter 2007 Financial Results", *Press Release*, (May 10, 2007), 3 pgs.

Poniard Pharmaceuticals, Inc., "Poniard Pharmaceuticals Reports Fourth Quarter and Year-end 2006 Financial Results and Corporate Update", *Press Release*, (Mar. 15, 2007), 3 pgs.

Poniard Pharmaceuticals, Inc., "Poniard Pharmaceuticals Reports Second Quarter 2006 Corporate Activities and Financial Results", *Press Release*, (Aug. 14, 2006), 3 pgs.

Poniard Pharmaceuticals, Inc., "Poniard Pharmaceuticals Reports Second Quarter 2007 Financial Results and Corporate Update", *Press Release*, (Aug. 7, 2007), 3 pgs.

Poniard Pharmaceuticals, Inc., "Poniard Pharmaceuticals Reports Third Quarter 2006 Corporate Activities and Financial Results", *Press Release*, (Nov. 14, 2006), 3 pgs.

Poniard Pharmaceuticals, Inc., "Poniard Pharmaceuticals Reports Third Quarter 2007 Financial Results and Corporate Update", *Press Release*, (Nov. 1, 2007), 4 pgs.

Poniard Pharmaceuticals, Inc., "Poniard Pharmaceuticals to Present Updated Results of Picoplatin Phase 2 Small Cell Lung Cancer Trial at 12th World Conference on Lung Cancer", *Press Release*, (Aug. 23, 2007), 2 pgs.

Raaphorst, G. P., et al., "Comparison of Human Tumour Cell Responses to Cisplatin and ZD0473 With and Without Irradiation", *Anticancer Research*, 24, 2004, 613-618.

Raynaud, F. I., et al., "*Cis*-Amminedichloro (2-Methylpyridine) Platinum (II) (AMD473), a novel sterically hindered platinum complex: In Vivo activity, Toxicology and Pharmacokinetics in mice", *Clinical Cancer Research*, 3(11), (1997), 2063-2074.

Raynaud, F. I., et al., "Biotransformation of AMD473, a Novel Platinum Analogue in Plasma, Cell Culture and Tissue" (Abstract 190), *Ann. Oncol.*, 9 (Suppl. 2), (1998), p. 50.

Roberts, D., et al., "Identification of Genes Associated With Platinum Drug Sensitivity and Resistance in Human Ovarian Cancer Cells", *British Journal of Cancer*, 92, (2005), 1149-1158.

Rochon, F. D., et al., "Iodo-bridged complexes of platinum(II) and synthesis of cis mixed-amine platinum(II) compounds.", *Can. J. Chem.* 64, 1894-1896 (1986)., (1986), 1894-1896.

Rochon, F. D., et al., "Multinuclear NMR spectra of [Pt(L)C13]—complexesand crystal structure of trans-Pt(2,6-di(hydroxymethyl)pyridine)$_2$Cl$_2$ 2H$_2$O", *Can. J. Chem.* 74, 2121-2130 (1996), 2121-2130.

Rochon, F. D., et al., "Synthesis and Studies of Pt(II) Compounds of the Types K[Pt(amine)Cl$_3$ ] and [Pt(amine)(acetonitrile)Cl$_2$]", *Inorganica Chemica Acta*, 143 (1988) 81-87., [CA: 108:214224x], (1988),81-87.

Rogers, P. M, et al., "In vitro combination studies with the sterically hindered platinum drug, ZD0473, in cisplatin-sensitive and resistant ovarian carcinoma cell lines", (Abstract 352), *Clin Cancer Res*, 6(Supp), Proceedings of the 2000 NCI/EORTC/AACR Symposium, (2000), p. 4537s.

Rogers, P. M, et al., "Preclinical combination studies in human ovarian carcinoma cell lines with the novel platinum complex ZD0473 (C/S-amminedichloro [2-methlypyridine] platinum(II) and paclitaxel", (Abstract P147), *Brit J Cancer Res. Meeting*, (Brighton UK), (2000), 1 pg.

Rogers, P., et al., "Sequence-Dependent Synergism Between the New Generation Platinum Agent ZD0473 and Paclitaxel in Cisplatin-Sensitive and—Resistant Human Ovarian Carcinoma Cell Lines", *European Journal of Cancer*, 38(12), (2002), 1653-1660.

Roman, L., et al., "Phase I study of picoplatin and docetaxel (D) with prednisone (P) in patients (pts) with chemotherapy-I metastatic hormone refractory prostate cancel!. (HRPC)", (Abstract 15546), *Journal of Clinical Oncology, 2007 ASCO Annual Meeting Proceedings Part I.* vol. 25, No. 18S (Jun. 20 Supplement), (2007), 2 pgs.

Rose, P. G., et al., "Second-Line Therapy With Paclitaxel and Carboplatin for Recurrent Disease Following First-Line Therapy With Paclitaxel and Platinum in Ovarian or Peritoneal Carcinoma", *Journal of Clinical Oncology*, 16(4), (1998), 1494-1497.

Rustin, G. J. S., et al., "Defining Response of Ovarian Carcinoma to Initial Chemotherapy According to Serum CA 125", *Journal of Clinical Oncology*, 14(5), (1996), 1545-1551.

Screnci, D., et al., "Relationships Between Hydrophobicity, Reactivity, Accumulation and Peripheral Nerve Toxicity of a Series of Platinum Drugs", *British Journal of Cancer*, 82(4), (2001), 966-972.

Sharp, S. Y., et al., "Lack of a Role for MRP1 in Platinum Drug Resistance in Human Ovarian Cancer Cell Lines", *Journal of Cancer*, 78(2), (1998), 175-180.

Sharp, S. Y, et al., "Non-cross resistance between oxaliplatin and ZD0473 in acquired oxaliplatin-resistant colon and ovarian carcinoma cell lines", (Poster 354) *Clin Cancer Res.*, 6(Supp), (2000), p. 4537s.

Sharp, S. Y., et al., "Retention of Activity by the New Generation Platinum Agent AMD0473 in Four Human Tumour Cell Lines Possessing Acquired Resistance to Oxaliplatin", *European Journal of Cancer*, 38, (2002), 2309-2315.

Smith, C. J., et al., "A Comparison of the Quantitative Methods for the Analysis of the Platinum-Containing Anticancer Drug {*cis*-[Amminedichloro(2-methylpyridine)]-platinum(II)} (ZD0473) by HPLC Coupled to Either a Triple Quadrupole Mass Spectrometer or an Inductively Coupled Plasma Mass Spectrometer", *Analytical Chemistry*, 75(6), (2003), 1463-1469.

Smith, M., et al., "Platinum Compounds in Cancer Therapy. Past, Present and Future", *Japanese Journal of Cancer and Chemotherapy*, 28(5), (w/ English Summary), (2001), 625-635.

Spenlehauer, G., et al., "Formation and Characterization of cisplatin loaded poly(d,*J*-lactide) microspheres for chemoembolization", (Abstract Only), *Journal of Pharmaceutical Sciences*, 75(8), (2006), 1 pg.

Stevenson, J. P., et al., "Pharmacokinetic (PK)/Pharmacodynamic (PD Trial of Novel Platinum Compound ZD0473 Administered as an IV Infusion Every 21 Days", (Abstract #450), *Proceedinis of ASCO; Clinical Pharmacology*, 20, (2001), 1 pg.

Stevenson, J. P., et al., "Pharmacokinetic/pharmacodynamic trial of the new generation platinum agent ZD0473 administered as an iv infusion every 21 days", (Poster #710), *Clin Cancer Res*, 7, (2001), p. 3796s Stewart, D. J., et al., "Phase I/Pharmacokinetic Study of ZD0473 and Docetaxel", (Abstract No. 423), *Proceedings, American Society of Clinical Oncology (ASCO 2002)*, vol. 21 (Part 1), (2002), 2 pgs.

Summa, N., et al., "Thermodynamic and Kinetic Studies on Reactions of Pt(11) Complexes With Biologically Revevant Nucleophiles", *Inorganic Chemistry*, 45, (2006), 2948-2959.

Sun, R. J., et al., "The growth inhibitory effect of ZD0473, a new generation platinum compound, is not influenced by mismatch repair proficiency", (Poster #4362), *Proceedings of the American Association for Cancer Research*, vol. 42,(2001), p. 813.

Takigawa, N., et al., "The combination effect of amrubicin with cisplatin or irinotecan for small-cell lung cancer cells", *Oncol Rep.*, 15(4), (Apr. 2006), 837-842.

Talman, E. G, et al., "Crystal and Molecular Structures of Asymmetric *cis*- and *trans*-Platinum (II/IV) Compounds and Their Reactions with DNA Fragements.", *Inorg. Chem.*1997, 36(5), 854-861., [CA 194433g]., (1997), 854-861.

Tannock, I. F., et al., "Docetaxel plus Prednisone or Mitoxantrone plus Prednisone for Advanced Prostate Cancer", *New England Journal of Medicine*, 351, (2004), 1502-1512.

Tikhonova, L S, et al., "Physicochemical Studies of Platinum(II) Hydroxylamine-containing Complexes with Nitrogen-containing Heterocyclic Ligands", *Russian Journal of Inorganic Chemistry*, 33(9), (1988), 1327-1329.

Tikhonova, L. S, et al., "Physicochemical studies of platinum (II) hydroxylamine-containing complexes with nitorgen containing heterocylic ligands", (No. 109: 242998t), *Chemical Abstracts*, 109(26), (Dec. 26, 1988), p. 841.

Treat, J., et al., "ZD0473 Treatment in Lung Cancer: An Overview of the Clinical Trial Results", *European Journal of Cancer*, 38 (uppl. 8), (2002), S13-S18.

Trigo, J. M., et al., "Phase I and Pharmacokinetic (PK) Study of Cis-Amminedichloro (2-Methylpyridine) Platinum (II) (ZA0473), a Novel Sterically Hindered Platinum Complex, in Patients (pts) with Advanced Solid Malignancies", (Abstract 648), *Proceedings, American Society of Clinical Oncology*, vol. 18, (1999), p. 169a Twelves, C., et al., "A Phase I Study of ZD0473 Combined With Paclitaxel for the Treatment of Solid Malignancies", *Cancer Chemotherapy & Pharmacology*, 52(4), (2003), 277-281.

Tyrrell, C, et al., "ZD0473 open-label phase II study in patients with metastatic hormone-refractory prostate cancer", (Abstract 2468), *Proc Am Soc Clin Oncol 21*, (2002), 2 pp.

Tyrrell, C., et al., "Open-Label Phase II Study of ZD0473 in Patients With Metastatic Hormone Refractory Prostate Cancer", (Abstract No. 814), *European Journal of Cancer*, vol. 37 (Suppl. 6), (2001), p. S222.

Tyrrell, C., et al., "Open-Label Phase II Study of ZD0473 in Patients With Metastatic Hormone-Refractory Prostate Cancer", (Abstract No. 622), *European Urology Supplements*, 1(1), (2002), p. 158

Tyrrell, C., et al., "Open-Label Phase II Study of ZD0473 in Patients with Metastatic Hormone-Refractory Prostate Cancer", (Poster 814), *ECCO 11*, (Lisbon, Spain, Oct. 2001), 1 pg.

Urien, S., et al., "Pharmacokinetics of Platinum After Oral or Intravenous Cisplatin: A Phase 1 Study in 32 Adult Patients", *Cancer Chemother. Pharmacol.*, 55, (2005), 55-60.

Vinje, J., et al., "NMR Spectroscopy of Anticancer Platinum Drugs", *Anticancer Agents Med Chem*, 7(1), (2007), 34-54.

Warren, M., et al., "Comparison of ZD0473- and cisplatin-DNA adducts with respect to damage recognition, translation synthesis, and mismatch repair", (Poster 3063), *American Association for Cancer Research (AACR)*, (New Orleans, LA), (2001), 1 pg.

Wong, E., et al., "Current Status of Platinum-Based Antitumor Drugs", *Chem. Rev.*, 99, (1999), 2451-2466.

Yamauchi, S., et al., "Additive Effects of Amrubicin with Cisplatin on Human Lung Cancer Cell Lines", *Osaka City Med J.*, 48(1), (Jun. 2002), 69-76.

Yan, J., et al., "Induced gene expression in SK-OV-3 cells treated with cisplatin or ZD0473, a novel non-cross resistant platinum complex", (Abstract 353), *Clin Cancer Res*, 6(Supp), Proceedings of the 2000 NCI/EORTC/AACR Symposium, (2000), p. 4537s.

Ziegler, C. J., et al., "High-Throughput Synthesis and Screening of Platinum Drug Candidates", *J. Biol. Inorg. Chem.* 5, (2000), 774-783.

Zieske, P. A., et al., "Characterization of cisplatin Degradation as affected by pH and Light", *American Journal of Hospitai Pharmacy*, vol. 48(7), (1991), 1500-1506.

"A Phase I Open-Label Study of Picoplatin in Combination With 5-Fluorouracil and Leucovorin as Initial Therapy in Subjects With Metastatic Colorectal Cancer", ClinicalTrials.gov archive, [online]. [Retrieved Jun. 19, 2010], (Jan. 20, 2009), 5 pgs.

"U.S. Appl. No. 11/935,979, Advisory Action mailed Jul. 13, 2010", 3 pgs.

"U.S. Appl. No. 11/935,979, Final Office Action mailed May 14, 2010", 11 pgs.

"U.S. Appl. No. 11/935,979, Response filed Jun. 17, 2010 to Final Office Action mailed May 14, 2010", 9 pgs.

"International Application No. PCT/US2010/34593, International Search Report mailed Sep. 8, 2010", 4 pgs.

"International Application No. PCT/US2010/34593, Invitation to Pay Additional Fee mailed Jul. 7, 2010", 8 pgs.

"International Application No. PCT/US2010/34593, Written Opinion mailed Sep. 8, 2010", 8 pgs.

Ciuleanu, T. E, et al., "Randomized Phase 3 study (SPEAR) of picoplatin + best supportive care (BSC) or BSC alone in patients with SCLC refractory or progressive within 6 months after 1st-line platinum-based chemotherapy.", (Abstract 7002), *J. Clin. Oncol., 28:7s, 2010 American Society of Clinical Oncology (ASCO) Annual Meeting*, (Chicago, Illinois, Jun. 4-8, 2010) (2010), 2 pgs.

De Jager, R., et al., "Results of a phase II study of picoplatin with docetaxel and prednisone in first-line treatment of castration-resistant prostate cancer (CRPC)", (Poster #5140), *2009 ASCO Annual Meeting*, (Orlando, FL, May 29-Jun. 2, 2009), (May 29, 2009), 1 pg.

Earhart, R. H., et al., "Picoplatin/5-fluroouracil/leucovorin (FOLPI) versus modified FOLFOX-6 as first line therapy for colorectal cancer (CRC)", (Abstract 345), *ASCO 2010 Gastrointestinal Cancers Symposium: Science and Multidisciplinary Management of GI Malignancies*, (Orlando, FL. Jan. 22-24, 2010), (Jan. 2010), 2 pgs.

Earhart, R, et al., "Randomized phase II study of picoplatin in combination with 5 fluorouracil and leucovorin (FOLPI) for colorectal cancer (CRC)", *J Clin Oncol* 27:15s, (Poster # 4026, *presented at 2009 ASCO Annual Meeting*, (Orlando, FL, May 29-Jun. 2, 2009), (2009), 1 pg.

Earhart, R. H, et al., "Randomized phase 2 study of picoplatin in combination with 5-fluorouracil and leucovorin (FOLPI) as a neuropathy-sparing alterative to modified FOLFOX-6 as first-line therapy for colorectal cancer (CRC)", (Abstract 4026), *J. Clin Oncol.*, 27, (Presented at *ASCO 2009 Gastrointestinal Cancers Symposium*, Orlando, FL, Jan. 22-24, 2009), (2009), p. 174s.

Earhart, R., et al., "Randomized phase II study of picoplatin in combination with 5 fluorouracil and leucovorin (FOLPI) for colorectal cancer (CRC).", *J Clin Oncol* 27:15s, (Poster # 4026, presented at *2009 ASCO Annual Meeting*, Orlando, FL, May 29-Jun. 2, 2009), (2009), 1 pg.

Ettinger, D. S, et al., "Phase II study of amrubicin as second-line therapy in patients with platinum-refractory small-cell lung cancer", *J Clin Oncol.*, 28(15), (May 20, 2010), 2598-2603.

Ettinger, D. S., et al., "Phase II Study of Amrubicin as Second-Line Therapy in Patients With Platinum-Refractory Small-Cell Lung Cancer," (published ahead of print as 10.1200/JCO.2009.26.7682 (*Journal of Clinical Oncology*)., (Apr. 12, 2010), 6 pgs.

Hess, V., et al., "Phase I study of carboplatin, doxorubicin and weekly paclitaxel in patients with advanced ovarian carcinoma", *Annals of Oncology* 14(4), (2003), 638-642.

Karlin, D. A., et al., "A dose-escalating phase I study of picoplatin with docetaxel and prednisone in chemotherapy-naive patients with metastatic hormone refractory prostate cancer (HRPC)", (Poster# 20403), *ASCO 2008 Genitourina Cancers Meeting*, 1 pg.

Karlin, D. A., et al., "Picoplatin as second-line therapy for patients with small cell lung cancer: A phase ii study", *Indian Journal of Cancer*, 45 Supplement), (Oct. 2008), p. S9.

Kim, Young Hak, et al., "Performance Status and Sensitivity to First-line Chemotherapy Are Significant Prognostic Factors in Patients With Recurrent Small Cell Lung Cnacer Receiving Second-ling Chemotherapy", *Cancer*, 113(9), (2008), 2518-2523.

Margiotta, N., et al., "Platinum(II) Complexes with Bioactive Carrier Ligands Having High Affinity for the Translocator Protein.", *J Med Chem.*, [Epub ahead of print], (Jun. 22, 2010), 11 pgs.

Mekhail, T. M, et al., "Paclitaxel in cancer therapy", *Expert Opin Pharmacother.*, 3(6), (Jun. 2002), 755-766.

More, S. S, et al., "Organic Cation Transporters Modulate the Uptake and Cytotoxicity of Picoplatin, a Third Generation Platinum Analogue", *Mol Cancer Ther*: 9(4), (Apr. 2010), 1058-1069.

Poniard Pharmaceuticals, Inc., "Poniard Announces Final Data from Phase 3 SPEAR Trial of Picoplatin in Small Cell Lung", *Press Release*, (Jun. 5, 2010), 3 pgs.

Poniard Pharmaceuticals, Inc., "Poniard Pharmaceuticals Provides Strategic Update on Picoplatin development Program", *Press Release*, (Mar. 24, 2010), 2 pgs.

Poniard Pharmaceuticals, Inc., "Poniard Pharmaceuticals Announces Results of Phase 3 SPEAR Trial of Picoplatin in Small Cell Lung Cancer to be Presented at the American Society of Clinical Oncology 2010 Annual Meeting", *Press Release*, (May 10, 2010), 1 pg.

Poniard Pharmaceuticals, Inc., "Poniard Pharmaceuticals Presents Positive Survival Data from a Phase 2 Clinical Study of Picoplatin in Metastatic Prostate Cancer at the 2010 ASCO Genitourinary Cancers Symposium", *Press Release*, (Mar. 5, 2010), 2 pgs.

Poniard Pharmaceuticals, Inc., "Poniard Pharmaceuticals to Present at the 12th Annual BIO CEO and Investor Conference", *Press Release*, (Feb. 5, 2010), 1 pg.

Poniard Pharmaceuticals, Inc., "U.S.Patent and Trademark Office Grants Reissue Patent on Picoplatin Composition of Matter", *Press Release*, (Mar. 18, 2010), 2 pgs.

Shepherd, F. A., et al., "Cyclophosphamide, Doxorubicin, and Vincristine in Etoposide- and Cisplatin-Resistane Small Cell Lung Cancer", *Cancer Treatment Reports*, 71(10), 941-944 (1987), (Oct. 1987), 941-944.

Singer, J. W; "Paclitaxel poliglumex (XYOTAX™, CT-2103): A macromolecular taxane", *J. Control Release*, 109(1-3), (Dec. 5, 2005), 120-126.

Subramanian, J., et al., "Continued lack of progress in SCLC", *Nature Reviews|Clinical Oncology*, 7, (Feb. 2010), 77-78.

Thayer, Ann M "Platinum Drugs take their Toll", *Chemical & Engineering News*, (Jun. 28, 2010), 24-28.

"U.S. Appl. No. 12/367,394, Preliminary Amendment filed Apr. 20, 2009", 6 pgs.

"Chinese Application Serial No. 200880011347.9, Office Action mailed Nov. 8, 2011", 10 pgs.

"Japanese Application Serial No. 2001-583780, Official Action mailed Aug. 26, 2011", (w/ English Translation), 12 pgs.

"Russian Application Serial No. 2009133447, Office Action mailed Nov. 25, 2011", 3 pgs.

"Taiwanese Application Serial No. 097124033, Response filed Nov. 9, 2011 to Office Action mailed Aug. 4, 2011", (w/ English Translation of Replacement Claims), 12 pgs.

"Ukrainian Application Serial No. 200909262, Office Action mailed Dec. 6, 2011", 3 pgs.

Hansen, R. M, et al., "Phase III study of bolus versus infusion fluorouracil with or without cisplatin in advanced colorectal cancer", *J Natl Cancer Inst.*, 88(10), (May 15, 1996), 668-674.

Icon Collaborators, "ICON2: randomised trial of single-agent carboplatin against three-drug combination of CAP (cyclophosphamide, doxorubicin, and cisplatin) in women with ovarian cancer. ICON Collaborators. International Collaborative Ovarian Neoplasm Study", *Lancet*,352(9140), (Nov. 14, 1998), 1571-1576.

Muggia, F. M, et al., "Phase III randomized study of cisplatin versus paclitaxel versus cisplatin and paclitaxel in patients with suboptimal stage III or IV ovarian cancer: a gynecologic oncologly group study", *J Clin Oncol.*, 18(1), (Jan. 2000), 106-115.

Skarlos, D. V. et al., "Carboplatin alone compared with its combination with epirubicin and cyclophosphamide in untreated advanced epitheliai ovarian cancer: a Hellenic co-operative oncology group study", *Eur J Cancer.*, 32A(3), (Mar. 1996), 421-428.

"U.S. Appl. No. 10/276,503, Final Office Action mailed Mar. 8, 2011", 32 pgs.

"U.S. Appl. No. 12/367,394, Non Final Office Action mailed Jul. 25, 2011", 17 pgs.

"U.S. Appl. No. 12/367,394, Response filed Jun. 2, 2011 to Restriction Requirement mailed May 5, 2011", 8 pgs.

"U.S. Appl. No. 12/367,394, Restriction Requirement mailed May 5, 2011", 6 pgs.

"U.S. Appl. No. 12/464,662, Non Final Office Action mailed May 6, 2011", 18 pgs.

"U.S. Appl. No. 12/508,372, Non Final Office Action mailed May 3, 2011", 18 pgs.

"U.S. Appl. No. 12/536,311, Response filed Aug. 16, 2011 to Restriction Requirement mailed Jul. 18, 2011", 12 pgs.

"U.S. Appl. No. 12/536,311, Restriction Requirement mailed Jul. 18, 2011", 12 pgs.

"U.S. Appl. No. 12/635,517, Restriction Requirement mailed Oct. 25, 2011", 13 pgs.

"Chinese Application Serial No. 200880011347.9, Office Action mailed Feb. 23, 2011", (w/ English Translation), 11 pgs.

"Chinese Application Serial No. 200880011347.9, Response filed Sep. 13, 2011 to Office Action mailed Feb. 23, 2011", (w/ English Translation), 18 pgs.

"Chinese Application Serial No. 200880011357.2, First Office Action mailed May 25, 2011", (w/ English Translation), 13 pgs.

"Chinese Application Serial No. 200880011357.2, Office Action Response filed Oct. 9, 2011", (w/ English Translation of Amended CI, 25 pgs.

"Chinese Patent Application Serial No. 200980109758.6, Voluntary Amendment filed Jul. 25, 2011", (w/ English Translation of Claims), 24 pgs.

"Chinese Patent Application Serial No. 200980110139.9, Voluntary Amendment filed Jul. 25, 2011", (w/ English Translation of Claims), 25 pgs.

"International Application Serial No. PCT/US2011/027264, International Search Report mailed May 9, 2011", 2 pgs.

"International Application Serial No. PCT/US2011/027264, Written Opinion mailed May 9, 2011", 4 pgs.

"Israeli Application Serial No. 200261, Office Action mailed Sep. 27, 2011", (w/ English Translation), 1 pg.

"Israeli Application Serial No. 200262, Office Action mailed Sep. 27, 2011", (English Translation), 1 pg.

"Taiwanese Application Serial No. 097124033, Office Action mailed Aug. 4, 2011", (w/ English Translation), 12 pgs.

Douillard, J. Y., et al., "A phase I study of oral uracil/tegafur (UFT) plus leucovorin (LV) combined with oxaliplatin in patients with metastatic colorectal cancer (CRC)", (Abstract 541), 11th NCI-EORTC-AACR Symposium on New Drugs in Cancer Therapy, (Nov. 7-10, 2000, Amsterdam), Supplement to Clinical Cancer Research, vol. 6, (2000), p. 4574s.

Earhart, R H, et al., "A phase I study of picoplatin in combination with 5-fluorouracil and leucovorin (FOLPI) for colorectal cancer (CRC): Comparison of two picoplatin schedules.", Earhart RH, Gladkov OA, Cheporov SV, Biakhov MY, Manikhas G, Berdov B, Tjulandian S, Breitz HB, De Jager RL. A phase I study of picoplatin in combination with 5-fluorouracil and leucovorin (FOLPI) for colorectal cancer (CRC): Comparison of two picoplatin s, (Apr. 18, 2009), Poster #3578.

Earhart, R., et al., "Randomized phase II study of picoplatin in combination with 5 fluorouracil and leucovorin (FOLPI) for colorectal cancer (CRC).", J Clin Oncol 27:15s, 2009, Poster # 4026, presented at 2009 ASCO Annual Meeting, Orlando, FL, May 29-Jun. 2, 2009., (2009), 1 pg.

Gross-Goupil, M., et al., "Topotecan (T) combined with oxaliplatin (OXA) every 3 weeks in cancer patients (pts): Final results of a phase I study", (Abstract 542), 11th NCI-EORTC-AACR Symposium on New Drugs in Cancer Therapy, (Nov. 7-10, 2000, Amsterdam), Supplement to Clinical Cancer Research, vol. 6, (2000), p. 4574s.

Long, D. F., et al., "Cisplatin: Chemistry, Distribution and Biotransformation", Biopharmaceutics & Drug Disposition, vol. 2, (Jan.-Mar. 1981), 1-14.

Muggia, F. M, et al., "Phase II study of liposomal doxorubicin in refractory ovarian cancer: antitumor activity and toxicity modification by liposomal encapsulation.", J Clin Oncol., 15(3), (Mar. 1997), 987-93.

Poniard Pharmaceuticals, Inc, "Poniard Pharmaceuticals and Allozyne Sign Definitive Merger Agreement", Press Release, (Jun. 22, 2011), 4 pgs.

Poniard Pharmaceuticals, Inc., "Poniard Pharmaceuticals Receives Chinese State FDA Approval for Clinical Development of Picoplatin", Press Release, (Mar. 1, 2011), 2 pgs.

Raaf, J. H, "Administration of chemotherapeutic agents Techniques and controversies", Support Care Cancer, 2, (1994), 335-346.

Stevenson, J. P, et al., "Phase I trial of the novel platinum analog ZD0473 administered in combination with gemcitabine to patients with advanced cancers", Clinical Cancer Research, 6, Meeting Abstract, (Nov. 2000), 540.

Trigo, J. M, et al., "Phase I and Pharmacokinetic (PK) Study of Cis-Amminedichloro (2-Methylpyridine) Platinum (II) (ZA0473), a Novel Sterically Hindered Platinum Complex, in Patients (pts) with Advanced Solid Malignancies", Proceedings, American Society of Clinical Oncology, vol. 18, (Abstract 648), (1999), p. 169a.

USE OF PICOPLATIN TO TREAT COLORECTAL CANCER

CROSS REFERENCES TO RELATED APPLICATIONS

This application is a continuation-in-part of Ser. No. 12/367,394 filed Feb. 6, 2009, which is in turn a continuation-in-part application of U.S. application Ser. No. 11/982,841, filed Nov. 5, 2007, now abandoned which claims the priority of U.S. Provisional Patent Applications, Ser. Nos. 60/857,066 (filed Nov. 6, 2006), 60/857,725 (filed Nov. 8, 2006), 60/877,495 (filed Dec. 28, 2006), 60/889,191 (filed Feb. 9, 2007), 60/931,589 (filed May 24, 2007), and 60/983,852 (filed Oct. 30, 2007), all of which are incorporated by reference herein in their entireties.

BACKGROUND OF THE INVENTION

Colorectal cancer remains the second most common cause of cancer-related death in the United States and a significant cause of cancer-related death in other countries as well.[1] For decades, the only approved chemotherapeutic drug for treatment of colorectal cancer was 5-fluorouracil (5-FU), and it continues to be the backbone of most first-line chemotherapeutic regimens for patients with advanced disease. However, there has been much progress made in treatment of colorectal cancer in the past decade, with the approval of several new therapeutic agents including irinotecan, oxaliplatin, capecitabine, and most recently, cetuximab and bevacizumab.[2,3] Importantly, a variety of new chemotherapeutic regimens utilizing these agents have been devised, which have led to increased response rates and incremental increases in the time to progression and median survival for patients with advanced disease.[2,3] Response rates for 5-FU/leucovorin, irinotecan, and oxaliplatin as single agent therapy have been low (23%, 18%, and 12%, respectively), progression-free survival has been short (median 4.0, 4.3, and 4.0 months, respectively), and median survival has also been short, approximately (12, 12, and 14.5 months, respectively).[4] With the introduction of 5-FU-based combination chemotherapeutic regimens using irinotecan and oxaliplatin, the response rate has increased substantially, with response rates reported as high as 64% (FOLFOX7), time to progression ranging from 8.9-12.3 months, and median survival now approaching approximately 20 months in some reports.[2-4]

Unfortunately, however, these newer combination chemotherapy regimens do have increased toxicity. Regimens containing irinotecan are associated with significant diarrhea and other gastrointestinal toxicity, while those containing oxaliplatin are associated with neurotoxicity.[2-10] The neurotoxicity observed is of two types: first, a cumulative and often dose limiting sensory loss with paresthesias that can interfere with function and second, a disturbing cold sensitivity that limits patient acceptance of the FOLFOX regimen.[7-10] Thus a drug of comparable efficacy without neurotoxicity would be a welcome substitute for oxaliplatin in combination with 5-FU and leucovorin.

Picoplatin is a platinum analogue that has demonstrated synergy with 5-FU in vitro in pre-clinical studies and has undergone extensive Phase 1 and 2 testing in a variety of cancers.[11-22] Like other platinum analogues, picoplatin causes cell death by the formation of covalent cross-links in DNA that interfere with DNA replication and transcription, leading to cell death. Cisplatin, the first platinum analogue, was introduced approximately 20 years ago and is still widely used. The approval of cisplatin was followed by approval of carboplatin, and most recently by that of oxaliplatin.

Treatment with platinum analogues is limited by their toxicity. While neurotoxicity and nephrotoxicity are the main dose-limiting toxicities (DLT) observed following cisplatin treatment, myelosuppression is most significant following carboplatin treatment. Carboplatin is known to cause cumulative dose-related toxicity that results in slow bone marrow recovery. Peripheral neurotoxicity is well documented in patients treated with oxaliplatin. The unacceptable nephrotoxicity, oto-, and neurotoxicity associated with earlier platinum analogues has not been reported with picoplatin either in animal studies or in clinical trials.[11, 19-22]

The efficacy of platinum analogues is also limited by several (intrinsic or acquired) mechanisms of resistance, including impaired cellular uptake, intracellular inactivation by thiols [e.g., reduced glutathione], and enhanced DNA repair and/or increased tolerance to platinum-DNA adducts.[23] Pre-clinical studies indicate that picoplatin can overcome these three mechanisms of resistance. This has been demonstrated in vitro and by using human ovarian xenograft tumor models that exhibit resistance to cisplatin.[13-17] Several human ovarian and colon cell lines with induced resistance to oxaliplatin retain sensitivity to picoplatin.[16-18]

In Phase 1 studies, indications of activity were seen in subjects with ovarian cancer, non-small cell lung cancer (NSCLC), small cell lung cancer (SCLC), head and neck cancer, renal cell cancer, thymic cancer, pancreatic cancer, stomach cancer, leiomyosarcoma, liver cancer, mesothelioma, and prostate cancers.[24,25] In Phase 2 studies, indications of efficacy were seen in subjects with ovarian, NSCLC, SCLC, mesothelioma, prostate cancer, and breast cancer.

Picoplatin and processes for making picoplatin and for using picoplatin in treatment are disclosed and claimed in U.S. Pat. Nos. 5,665,771 (issued Sep. 9, 1997), and 6,518,428 (issued Feb. 11, 2003), and in PCT/GB0102060, filed May 10, 2001, published as WO2001/087313, which are incorporated herein by reference in their entireties.

About 40% of patients with mCRC have K-ras mutations and their mCRC does not respond to epidermal growth factor receptor (EGFR) inhibitors such as cetuximab and panitumumab. Many cetuximab-treatment studies in mCRC demonstrated very low or even zero response rates, short progression-free survival, and short overall survival in K-ras mutation positive mCRC. Because K-ras wild type CRC patients treated with EGFR inhibitors have significantly higher objective response rates, increased progression-free survival, and increased overall survival, K-ras testing is now used in routine clinical practice to select the subset of mCRC patients most likely to benefit from treatment with an EGFR inhibitor. Subset selection spares patients who are unlikely to respond to EGFR inhibitors for side effects and the cost of an ineffective drug. Examples of companies that offer K-ras testing to medical oncologists include:

For example, see: M. Brink et al., Carcinogenesis. 2003; 24:703-10; A. Lièvre et al., J Clin Oncol. 2008; 26:374-9; W. De Roock et al., Ann Oncol. 2007, Nov. 12; F. Di Fiore et al., Br J. Cancer. 2007; 96:1166-9; A. Lièvre et al., Cancer Res. 2006; 66:3992-5; C. S. Karapetis et al., NEJM. 2008; 359 (N 17):1757-1765; Amado et al., 2008 American Society of Clinical Oncology Gastrointestinal Cancers Symposium, Abstract 278.

Picoplatin (SP-4-3) (cis-aminedichloro(2-methylpyridine) Pt(II)), and useful prodrugs and analogs thereof are disclosed in U.S. Pat. Nos. 5,665,771; 6,518,428; 6,413,953 and PCT/GB/01/02060.

SUMMARY OF THE INVENTION

An embodiment of the present invention provides a method of treatment of colorectal cancer, comprising administering to a patient afflicted with colorectal cancer picoplatin, 5-fluorouracil (5-FU), and leucovorin, wherein 5-FU and leucovorin are administered intravenously at least twice at intervals of about 2-6 weeks and the picoplatin is administered with the leucovorin and 5-FU every other time that the fluorouracil and leucovorin are administered.

Another embodiment of the invention provides a method of treatment of colorectal cancer, comprising administering to a patient afflicted with colorectal cancer effective amounts of a combination of picoplatin, 5-FU and leucovorin, wherein the picoplatin, 5-FU and leucovorin are administered intravenously at least twice at intervals of about two weeks, wherein the amount of picoplatin is less than the maximum tolerated dose of picoplatin when administered in said combination.

Another embodiment of the invention provides a method of treatment of colorectal cancer, comprising administering to a patient afflicted with colorectal cancer picoplatin, 5-FU, and leucovorin, wherein 5-FU and leucovorin are administered intravenously at intervals of about two weeks, and the picoplatin is administered with the leucovorin and 5-FU every time that the fluorouracil and leucovorin are administered, wherein the picoplatin is administered at a dose of about 45-120 mg/m$^2$.

In various embodiments of the present method, the patient has not previously been treated for metastatic disease, or the patient has not previously had systemic treatment, such as chemotherapy, for localized or metastatic disease. For example, the patient may have had surgery to remove, or to de-bulk the primary tumor or to resect the portion of the colon or rectum comprising the tumor and then can be treated with one of the picoplatin, 5-FU, leucovorin regimens (e.g., FOLPI) of the invention to treat any remaining primary tumors or metastatis, and/or to prevent or delay progression of the cancer, including to prevent or delay the development of metastases. The patient may have received earlier chemotherapy at the time of primary tumor treatment, e.g., at least 6 months prior to the present picoplatin treatment. Following picoplatin treatment, a patient, such as one responsive to picoplatin, may undergo resection of the primary lesion or metastases on other organs or tissues. In one embodiment, the primary tumor is resected or debulked following administration of picoplatin, 5-FU and leucovorin, while in another embodiment, the patient has previously (e.g., prior to administration of picoplatin, 5-FU and leucovorin) had surgery to resect or de-bulk a colorectal tumor.

In various embodiments, the picoplatin can be administered with curative intent, rather than merely seeking to arrest the disease with no remission. The dosage of the picoplatin can be increased beyond that bringing about disease stasis in order to achieve a cure in the patient, including complete response of both the primary colorectal tumor(s) and any metastases.

The picoplatin and the leucovorin can be administered concurrently in any treatment cycle where picoplatin is administered.

In another embodiment of the invention, the picoplatin is administered substantially concurrently with the leucovorin and the picoplatin is administered at every second treatment of the patient with the 5-FU and the leucovorin, e.g., every four weeks. The leucovorin can be administered at a dosage of about 250-500 mg/m$^2$, preferably at about 400 mg/m$^2$. The picoplatin is administered at a dosage of about 60-180 mg/m$^2$. The 5-FU is administered at a total dosage of about 2500-3000 mg/m$^2$. A preferred treatment cycle for leucovorin and 5-FU is every two weeks, and picoplatin is administered every 4 weeks, e.g., at a low dose of about 60-75 mg/m$^2$, e.g., 60 mg/m$^2$, or at a high dose of about 120-180 mg/m$^2$, preferably about 120-150 mg/m$^2$, e.g. about 150 mg/m$^2$.

Therefore, in one embodiment of the invention, the leucovorin, at a dosage of 250-500 mg/m$^2$, is administered as an about 2 hour infusion concurrently with the picoplatin, when it is given, wherein the picoplatin dosage is 120-180 mg/m$^2$, e.g., about 150 mg/m$^2$; the administration of the leucovorin and the picoplatin being followed by a 5-FU dosage of about 400 mg/m$^2$ as a bolus; the 5-FU dosage being followed by 5-FU at a dosage of 2,400 mg/m$^2$, preferably administered as a 46 hour continuous infusion, wherein the leucovorin and 5-FU are provided to the patient at intervals of two weeks and the leucovorin, picoplatin, and 5-FU are provided to the patient at alternating intervals of four weeks. In another embodiment, a low dose of picoplatin of about 45-75 mg/m$^2$, e.g., about 60-75 mg/m$^2$, e.g., about 60 mg/m$^2$, is administered.

In another embodiment of the invention, the leucovorin, at a dosage of 400 mg/m$^2$, is administered as a 2 hour infusion; the administration of the leucovorin being followed by a 5-FU bolus at a dosage of 400 mg/m$^2$; the 5-FU bolus dosage being followed by parenteral 5-FU at a dosage of 2,400 mg/m$^2$, preferably administered as a 46 hour continuous infusion; the administration of the leucovorin and the 5-FU taking place every two weeks; wherein every two weeks picoplatin, at a dosage of up to about 50 mg/m$^2$, e.g., at about 40-50 mg/m$^2$, e.g., about 45 mg/m$^2$, is administered concurrently with the leucovorin, preferably simultaneously. Picoplatin dosages of about 45-105 mg/m$^2$ can also be administered.

It has unexpectedly been found that, in some cases, the combination of low doses of picoplatin administered with leucovorin and 5-FU at every treatment cycle, are as effective as, or more effective than, higher doses, e.g., the MTD, given at the same intervals, in producing a response. The MTD for the 2 week and 4 week picoplatin administration schedules (see Table 1) are discussed below. Preferably, such doses in the initial treatment are lower or substantially lower than the MTD. Such doses can range from about 40-60 mg/m$^2$ of picoplatin every two weeks, given with leucovorin and followed by 5-FU, as discussed below.

It has surprisingly been found that a total cumulative dose in excess of about 900 mg/m$^2$ can be tolerated by patients without neuropathy of Grade 2 or higher being observed.

As used herein, the term "concurrently" means that the administrations are simultaneous, overlapping or close enough in time so that the two or more agents administered are present in vivo in therapeutically effective amounts.

The present method also can comprise administration of an effective amount of a 5-HT$_3$ receptor antagonist, as an antiemetic.

The present invention also provides a method comprising administering picoplatin in a dosage form comprising an isotonic solution comprising water, a tonicity adjuster, and about 0.5 mg/mL dissolved picoplatin. The dosage form can also comprise an effective amount of dissolved or dispersed 5-FU and/or leucovorin in accord with the doses disclosed herein. The dosage form also does not contain a preservative or bacteriostatic agent. An appropriate volume of the dosage form can be administered to achieve a desired therapeutic dose.

The dosage form also can comprise a first container comprising the picoplatin solution and a second container comprising a solution of leucovorin. The two containers can further comprise means to simultaneously administer the contents to a patient, e.g., the containers can be plastic intravenous bags that can be independently connected to a single intravenous tube so that the content of each container can be simultaneously administered to the patient, e.g., via a Y-link. These containers can be packaged together with instructions regarding their end-use, e.g., in a kit.

In various embodiments, the invention provides a method for selecting a regimen of treatment for a patient afflicted with mCRC comprising: (a) identifying a patient afflicted with mCRC, (b) determining if the mCRC comprises a wild type K-ras gene or a mutated K-ras gene and (c) if the mCRC comprises a K-ras mutation positive genotype, then administering to the patient picoplatin and, optionally, 5-FU and leucovorin.

DETAILED DESCRIPTION OF THE INVENTION

The use of picoplatin to treat metastatic colorectal cancer will be conducted in three parts. Phase 1 is a dose escalation study to identify the maximum tolerated dose (MTD) of picoplatin that can be administered either every two weeks or every four weeks, with 5-FU and leucovorin (LV) administered every two weeks, as initial therapy for subjects with metastatic colorectal cancer who have not been previously treated for metastatic disease. Phase 2 is a randomized study. In one arm of the study, picoplatin is tested at the MTD and selected schedule (every four weeks) combined with 5-FU and leucovorin that are administered every two weeks, to assess safety and efficacy. In the other arm, picoplatin will be substituted for oxaliplatin in a modified FOLFOX 6 regimen wherein the 100 mg/m$^2$ oxaliplatin dose in FOLFOX 6 has been reduced to 85 mg/m$^2$, and administered every 2 weeks, so that the two agents can be compared in the context of a widely used regimen. It is believed that cancer patients can be more effectively treated with the regimen of the present invention, which employ picoplatin instead of cisplatin, carboplatin or oxaliplatin, because they will experience fewer side effects, such as neuropathy, while preferably receiving higher doses of the platinum (Pt) drug.

Subjects eligible for the Phase 1 study will have Stage 1V colorectal cancer and will have received no systemic therapy for metastatic cancer. Prior adjuvant chemotherapy with a 5-FU-based treatment regimen not containing oxaliplatin or irinotecan is acceptable if there has been a treatment-free interval of at least 6 months.

Phase 1

Subjects are assigned centrally to treatment with picoplatin administered either every two or every four weeks and are assigned a dose of picoplatin to be given dependent on the study results to date. Each patient also receives 5-FU and leucovorin therapy every two weeks. Cohorts of 3 subjects receive their assigned dose of picoplatin and leucovorin and 5-FU according to the following schedule:

Day 1: Picoplatin, assigned dosage, as a 2-hour infusion, given either every cycle of 5-FU and leucovorin (q 2 weeks, Schedule A) or with every other cycle of 5-FU and leucovorin (q 4 weeks, Schedule B). Leucovorin, 400 mg/m$^2$ in D5W (water-5% dextrose), will be administered as a 2 hour infusion, either alone or, if the patient is to receive picoplatin, at the same time as picoplatin in separate bags using a Y-line. The leucovorin (±picoplatin) will be followed by a 5-FU bolus=400 mg/m$^2$ and then by 5-FU, 2,400 mg/m$^2$ in D5W administered as a 46 hour continuous infusion.

Subjects in Phase 1 are centrally assigned to one of two schedules of picoplatin. The first cohort of q 2 week (Schedule A) subjects are treated with picoplatin at a dosage of 45 mg/m$^2$, every cycle, q 2 weeks. Subsequent sequential cohorts of subjects assigned to this schedule receive picoplatin at dose levels increasing by 15 mg/m$^2$ if treatment is well tolerated to 75 mg/m$^2$ and then by 5 mg/m$^2$ to 90 mg/m$^2$, and finally by 15 mg/m$^2$ to 135 mg/m$^2$ until unacceptable dose-limiting toxicity (DLT) establishes the MTD.

The MTD is defined as the dose of picoplatin below the dose at which at least one third of at least 6 subjects experience a DLT. Tolerance data from only the first 4 weeks of treatment is used to determine the MTD. Thus, data following the first two doses of picoplatin in the q 2 week (Schedule A) subjects and following only the first dose of picoplatin in the q 4 week (Schedule B) subjects are considered. The first cohort of q 4 week (Schedule B) subjects will be treated with picoplatin at a dosage of 60 mg/m$^2$, every other cycle, q 4 weeks. Subsequent sequential cohorts of subjects assigned to this schedule will receive picoplatin at dose levels increasing by 30 mg/m$^2$ if treatment is well tolerated and until unacceptable dose-limiting toxicity (DLT) establishes the MTD. Depending on the pattern and severity of toxicity observed, additional intermediate dose levels of either schedule of picoplatin administration may be studied.

Within each schedule, the cohort size is 3 subjects, and is expanded to 6-10 subjects if a DLT is observed. Within each cohort of each schedule, one patient is treated initially; if no DLT is observed within the following 4 weeks (2 drug cycles), the remaining two subjects may be treated. If a DLT is observed in the first patient within a cohort, whether or not to proceed with enrollment of additional subjects in the cohort will be determined on a case-by-case basis. All subjects within a q 2 week (Schedule A) cohort will have completed 2 cycles (a cycle=the 2-day treatment regimen and an additional 12-day follow-up period) prior to escalating the dose in the next cohort of subjects. All subjects within a q 4 week (Schedule B) cohort will have completed 1 cycle of the 2-day treatment regimen (which should include 5FU/leucovorin) and an additional 26-day follow-up period prior to escalating the dose in the next cohort of Schedule B subjects.

If no DLT is observed among the 3 subjects within a cohort, picoplatin dose escalation may proceed in the next cohort of that schedule of picoplatin. If one DLT is observed, the cohort size at the specified dose and schedule of picoplatin is expanded to 6-10 subjects. Additional subjects may be entered at any dosage level and schedule below the dose at which 2 of 6 have DLT to obtain additional safety or efficacy data.

Phase 2

The dose of the Phase 2 component of this study is selected based on the dose intensity of picoplatin achieved on each dose and schedule, the number of cycles tolerated and a subjective assessment of the tolerability and safety profile of each dose and schedule and a preliminary assessment of response rate in accord with Phase 1. The schedule for Phase 2 is selected as Schedule B, the q 4 week schedule. The subjects (approximately 100 with metastatic CRC, at about 25 clinical sites) are randomized to the modified FOLFOX 6[6] or to FOLPI-150.

The FOLPI regimen is as follows:

Picoplatin 150 mg/m$^2$, is administered with every alternate cycle of 5-FU and leucovorin (q 4 weeks, Schedule B) as a 2 hour infusion. Leucovorin (400 mg/m$^2$ in D5W) is administered every 2 weeks as a 2-hour infusion, either alone, or given at the same time as the picoplatin in a separate bag using a Y-line. The administration of leucovorin±picoplatin is followed by a 5-FU bolus of 400 mg/m$^2$ and then by 5-FU, 2400 mg/m$^2$ in D5W administered as a 46 hour continuous infusion.

The modified FOLFOX 6 regimen is as follows:

Oxaliplatin 85 mg/m², as a 2-hour infusion is administered every 2 weeks. Leucovorin (400 mg/m² in D5W) is administered every 2 weeks as a 2-hour infusion. Oxaliplatin is given at the same time as the leucovorin in a separate bag using a Y-line. The administration of leucovorin+oxaliplatin is followed by a 5-FU bolus of 400 mg/m² and then by 5-FU, 2400 mg/m² in D5W administered as a 46 hour continuous infusion.

Neuropathy assessment is performed at baseline and after every two cycles of therapy (approximately every month) by an independent neurologist. The subject and the neurologist are not informed whether the platinum infused is oxaliplatin or picoplatin. This assessment by the neurologist is used to determine the incidence of Grade 2 or greater peripheral neuropathy. In Phase 2, for the purpose of determining toxicity for dose reduction or study drug discontinuation, the treating physician performs a neurological assessment using the NCI CTCAE. These CTCAE criteria are used to determine the need to dose reduce prior to each cycle. The assessment of the neurologist is used for determination of the safety endpoint, the incidence of neuropathy, and is performed independently every other cycle using the protocol-specified neuropathy scale, but is not be used for dose modification. For all subjects, hematology and serum chemistry laboratory studies are obtained prior to each treatment cycle. Treatment cycles (5-FU and leucovorin±picoplatin or oxaliplatin depending on schedule) are repeated every 2 weeks, but may be delayed up to 2 weeks while awaiting recovery of clinical or laboratory abnormalities. Data from all cycles of treatment and cumulative toxicity are assessed for safety analysis.

Tumor evaluations will be done at baseline and after every 4th treatment of 5-FU/leucovorin (every 8 weeks, unless doses have been delayed) on study. The efficacy endpoint will include objective response rate according to RECIST criteria.[26] Duration of response, time to progression, progression-free survival, and overall survival are also evaluated.

The demographics and study treatments are summarized in Table 1A, 1B and 1C, below:

TABLE 1A

Patient Demographics

| | | Q4W n = 18 | Q2W n = 55 |
|---|---|---|---|
| Age (in years) | Median (range) | 60 (34, 75) | 58 (42, 70) |
| Age Group | <65 | 67% | 75% |
| | ≧65 | 33% | 26% |
| ECOG PS | 0 | 39% | 24% |
| | 1 | 61% | 76% |
| Prior Chemotherapy | Yes | 6% | 16% |
| Original Site of Disease | Colon | 50% | 56% |
| | Rectum | 44% | 42% |
| | Colon + Rectum | 6% | 2% |
| # of Metastatic Sites | Median (range) | 2 (1-5) | 2 (1-5) |
| Sites of Metastatic Disease | Liver | 72% | 86% |
| | Peritoneum/pelvic/abdomen | 33% | 24% |
| | Lung | 33% | 44% |
| | Lymph nodes | 44% | 40% |
| | Ascites | 22% | 13% |
| | Skin/soft tissue | 6% | 0 |
| | Pleural effusion | 17% | 4% |
| | Other | 0 | 6% |

TABLE 1B

Phase 1 (Dose Escalation)

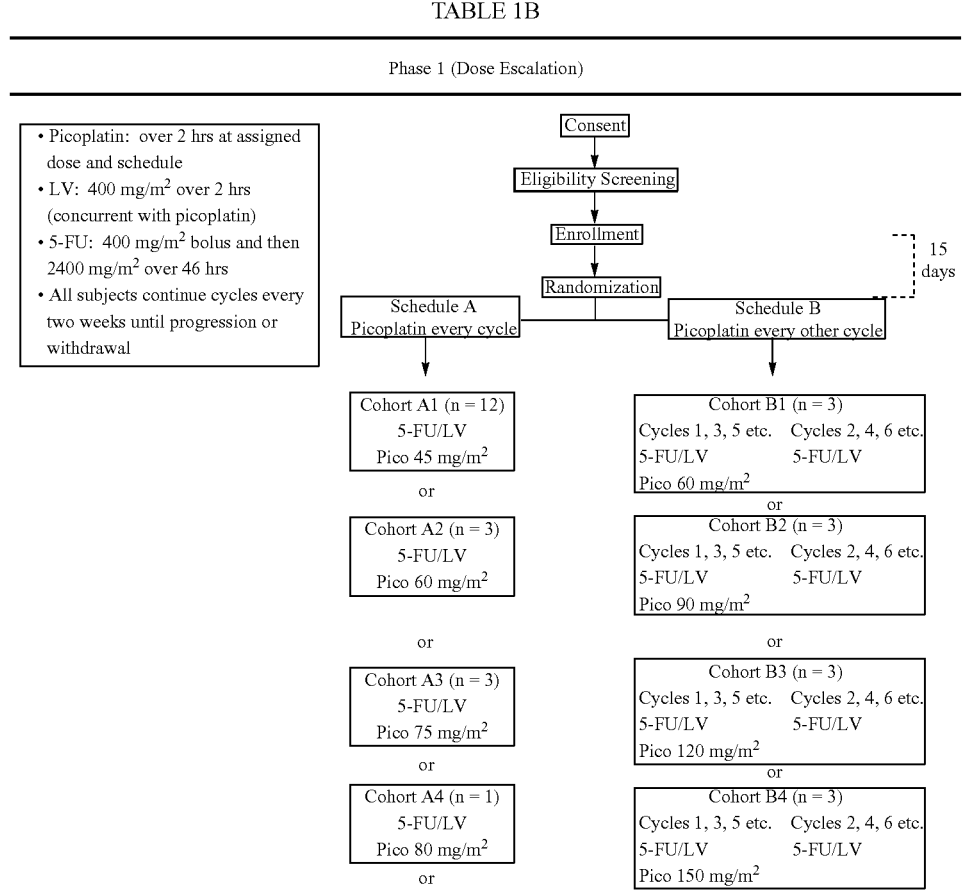

TABLE 1B-continued

Phase 1 (Dose Escalation)

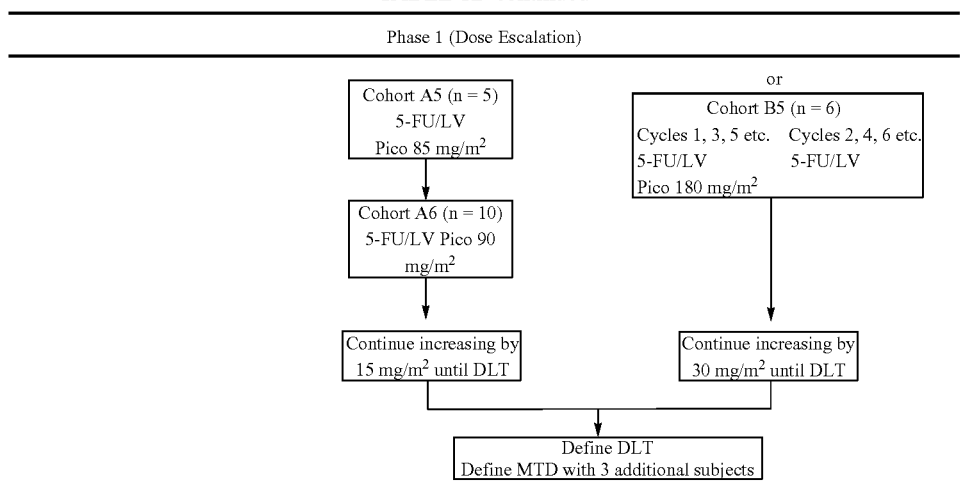

TABLE 1C

Phase 2

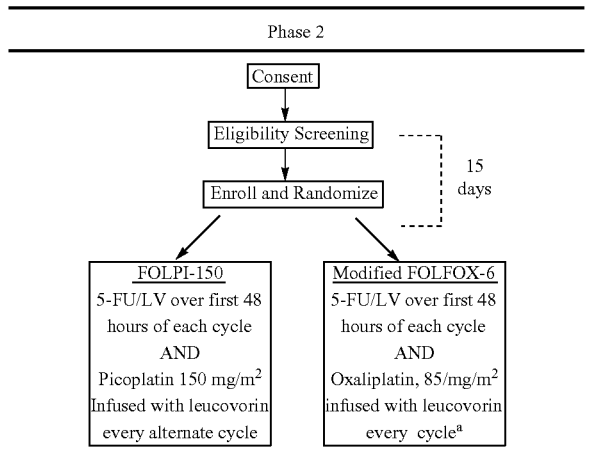

[a] Picoplatin: over 2 hours 150 mg/m$^2$; oxaliplatin: 85 mg/m$^2$, over 2 hours; LV: 400 mg/m$^2$ over 2 hours (concurrent with picoplatin when given or oxaliplatin) followed by 5-FU: 400 mg/m$^2$ bolus and then 2400 mg/m$^2$ over 46 hours. All subjects continue cycles every two weeks until progression or discontinuation of study drug due to toxicity.

Selection of Picoplatin Dose

Picoplatin was generally tolerated in combination with other myelosuppressive chemotherapeutic agents in previous Phase 1 studies at doses of 120-150 mg/m$^2$ administered every 3 weeks, i.e., doses equivalent to 80-100 mg/m$^2$ every 2 weeks or 160-200 mg/m$^2$ administered every 4 weeks. None of these studies, however, studied picoplatin in combination with 5-FU and leucovorin. 5-FU/leucovorin is not generally myelotoxic and thus the doses of picoplatin selected as the initial starting doses in the dose escalation portions of the current study, i.e., 45 mg/m$^2$ every two weeks and 60 mg/m$^2$ every four weeks, were well below the expected MTDs of picoplatin administered on these schedules.

Administration of Picoplatin

Investigational-site staff must use standard cytotoxic handling procedures when preparing picoplatin for administration. Picoplatin is supplied as a ready-to-use formulation. The contents of the vials must be transferred to a suitable bag for administration. The compatibility of the formulation with typical infusion equipment has been assessed, and results have established compatibility with EVA infusion bags, PVC infusion tubing, and polypropylene syringes when the materials are protected from light. PVC infusion bags are not recommended for administration of picoplatin.

The compatibility of the formulation with typical administration sets has been assessed, and limits of acceptability have been set as 8 hours in a covered infusion bag. The product is highly sensitive to light and should not be exposed to ambient light for more than 1 hour without light protection. The bag must be protected from light during preparation and administration at the time of use.

There is no preservative or bacteriostatic agent present in the picoplatin formulation. Therefore, picoplatin must be transferred under aseptic conditions. The solution must be completely used or discarded within 8 hours of introduction into an infusion bag. As with all platinum complexes, contact with aluminum should be avoided.

Picoplatin should be administered by peripheral vein or central line; it must not be given by the intramuscular or subcutaneous route. The starting dose will be calculated based on the body surface area from the height and weight of the patient. If the patient's weight changes by more than 10%, the treating physician must recalculate the body surface area and amend the dose.

Picoplatin should be administered over 2 hours. It should be administered concurrently with leucovorin, in separate bags using a Y-line, when the two drugs are to be given on the same day. These two drugs have been tested and shown to be compatible when administered in this manner.

Subjects also received anti-emetic therapy consisting of a 5-HT$_3$ receptor antagonist plus dexamethasone 30 minutes prior to a dose of picoplatin. Subjects may also receive anti-emetic therapy for several days following treatment, which may include oral lorazepam, prochlorperazine, or equivalent for up to 7 days, as clinically indicated for breakthrough nausea and/or vomiting.

Guidance for Administration

Detailed guidance for administration of 5-FU and leucovorin are provided in the product labels. Briefly, leucovorin 400 mg/m$^2$ IV infusion in D5W will be administered over 2 hours at the same time as picoplatin (if picoplatin is to be given on that day), in separate bags using a Y-line, followed by a bolus of 5-FU=400 mg/m$^2$ and then by 5-FU 2,400 mg/m$^2$ in D5W (recommended) administered as a 46-hour continuous IV infusion.

Dose Modifications

Dose Modification of Picoplatin

Dose-reduction is mandatory if any of the following hematological events are observed during the previous cycle: absolute neutrophil count (ANC)<0.5×10$^9$/L for at least 5 days; absolute neutrophil count<1.0×10$^9$/L complicated with Grade≧2 fever (>38.5° C.); platelet count <25×10$^9$/L; not reaching a platelet count≧100×10$^9$/L and ANC≧1.5×10$^9$/L by Day 15.

Dose reduction is also required for any treatment events involving any treatment-related Grade 3 toxicity, any Grade 4 toxicity, or any renal toxicity or neurotoxicities as described below.

For subjects receiving picoplatin every 2 weeks, the dose reduction should be 15 mg/m$^2$; for subjects receiving picoplatin every 4 weeks the dose reduction should be 30 mg/m$^2$.

Dose Reduction in the Event of Serum Creatinine Changes

Serum creatinine should be measured before every dose of picoplatin. For subjects with abnormal serum creatinine, the dose of picoplatin (but not 5-FU or leucovorin) should be modified according to the following Table 2 in Phase 1:

TABLE 2

| Serum Creatinine Value | Dose modification for q 2 week (Schedule A) picoplatin subjects | Dose modification for q 4 week (Schedule B) picoplatin subjects |
|---|---|---|
| ≦institutional ULN | recommended dose | recommended dose |
| >1.0 to 1.5 times ULN | reduce by 25% | reduce by 25% |
| >1.5 to 2.0 times ULN | reduce by 50% | reduce by 50% |
| >2.0 times ULN | discontinue treatment with picoplatin | discontinue treatment with picoplatin |

In Phase 2, the following dose reductions are recommended for elevated serum creatinine (Table 3):

TABLE 3

| Serum creatinine | Dose modification for Phase 2 FOLPI subjects |
|---|---|
| ≦institutional ULN | recommended dose |
| >1.0 to 1.5 times ULN | reduce by picoplatin 30 mg/m$^2$ |
| >1.5 to 2.0 times ULN | reduce by picoplatin 60 mg/m$^2$ |
| >2.0 times ULN | discontinue treatment with picoplatin |

Dose Modification in the Event of Neurotoxicity

The dose of picoplatin should be modified according to the CTCAE grade of toxicity and its duration as shown on Table 4:

TABLE 4

| | Duration of Toxicity | |
|---|---|---|
| Toxicity Grade | Resolves before next cycle | Persistent (present at start of next cycle) |
| Grade 1 | No change | Maintain picoplatin dose |
| Grade 2 | No change | Reduce picoplatin dose by 30 mg/m$^2$ |
| Grade 3 | Reduce picoplatin dose by 30 mg/m$^2$ | Discontinue picoplatin |
| Grade 4 | | Discontinue picoplatin |

Up to three dose reductions of a 30 mg/m$^2$ may occur should toxicity not improve or worsen at a later cycle.

Dose Modification of 5-FU

The first time the dose of picoplatin is reduced, the bolus dose of 5-FU should be omitted. The second time the dose of picoplatin is reduced, the infusional dose should be reduced by 600 mg/m$^2$. Once decreased, the reduced dose of 5-FU should be continued; i.e., the dose of 5-FU should not be subsequently increased.

If the platelet count or ANC count is Grade 1 or 2 at day 15 in a cycle with picoplatin, and the subject receives the alternate i.e., even numbered cycle that does not include picoplatin, the dose of 5-FU should not be reduced at this cycle. At the next treatment cycle, the doses of picoplatin and 5-FU should be reduced by one level. Dose modifications for Grade 3 or 4 non-hematological events must be made. Continue treatment only once toxicity has resolved to <Grade 3.

Dose Modification of Leucovorin

There are no dose modifications for leucovorin, unless drug sensitivity is suspected because of a temporal relationship to the time of leucovorin administration.

Results

The total picoplatin exposed in Phase 1 study is summarized below on Table 5.

TABLE 5

| Dose Level | n | Cycles* (median, range) | Cumulative Dose, mg/m$^2$ (median, range) | Dose Intensity, mg/m$^2$/wk (median, range) | Relative Mean Dose Intensity (%) |
|---|---|---|---|---|---|
| Q4W | | | | | |
| 60 mg/m$^2$ | 3 | 16 (4-20) | 301 (120-543) | 13 (8-15) | 87 |
| 90 mg/m$^2$ | 3 | 24 (14-28) | 755 (480-902) | 16 (13-18) | 83 |
| 120 mg/m$^2$ | 3 | 4 (4-24) | 240 (240-630) | 28 (12-29) | 86 |
| 150 mg/m$^2$ | 3 | 7 (4-11) | 670 (300-870) | 32 (31-32) | 81 |
| 180 mg/m$^2$ | 6 | 6 (2-46) | 386 (180-1470) | 35 (5-43) | 76 |
| Q2W | | | | | |
| 45 mg/m$^2$ | 12 | 12 (2-30) | 343 (90-1144) | 16 (7-22) | 82 |
| 60 mg/m$^2$ | 3 | 5 (4-24) | 211 (210-966) | 20 (19-23) | 76 |
| 75 mg/m$^2$ | 3 | 10 (5-12) | 529 (331-826) | 24 (24-32) | 79 |
| 80 mg/m$^2$ | 1 | 30 | 1145 | 19 | 77 |
| 85 mg/m$^2$ | 5 | 8 (1-16) | 420 (85-659) | 23 (13-41) | 80 |
| 90 mg/m$^2$ | 10 | 8 (3-26) | 435 (210-960) | 23 (12-44) | 69 |
| 105 mg/m$^2$ | 12 | 8 (4-28) | 475 (270-1871) | 27 (12-52) | 67 |
| 120 mg/m$^2$ | 3 | 8 (3-12) | 668 (315-780) | 41 (26-44) | 73 |
| 135 mg/m$^2$ | 6 | 8 (4-15) | 480 (360-914) | 38 (11-58) | 70 |

*A cycle equals a dose of 5-FU/LV and a follow-up period of 2 weeks, with or without picoplatin.

73 patients have been treated to date in Phase 1. In the q 2 w schedule, 1 of 6 patients showed a DLT of Grade 4 thrombocytopenia and neutropenia at a picoplatin dose level of 105 mg/m$^2$. The MTD for the q 2 w schedule was determined to be 85 mg/m$^2$. In the q 4 w schedule, DLT was observed at 180 mg/m$^2$ in 2 of 6 patients. The MTD was determined to be 150 mg/m$^2$. Patients have received up to 24 cycles and the therapy was well tolerated.

For both schedules, dose delays were primarily from neutropenia or thrombocytopenia, with increased hematological toxicity observed at higher doses as shown on Table 6, below.

TABLE 6

| Hematological Toxicity | | | |
|---|---|---|---|
| Lab | Worst Grade | Q4W (n = 18) | Q2W (n = 55) |
| ANC* | 1 | 0 | 2% |
| | 2 | 17% | 15% |
| | 3 | 22% | 38% |
| | 4 | 39% | 31% |
| Platelets | 1 | 22% | 35% |
| | 2 | 28% | 27% |
| | 3 | 17% | 15% |
| | 4 | 22% | 13% |

TABLE 6-continued

Hematological Toxicity

| Lab | Worst Grade | Q4W (n = 18) | Q2W (n = 55) |
|---|---|---|---|
| Hemoglobin | 1 | 17% | 29% |
| | 2 | 44% | 46% |
| | 3 | 22% | 11% |
| | 4 | 6% | 6% |

*1 patient on each arm had grade 3 febrile neutropenia

Grade 3 non-hematological toxicities related to treatment are summarized on Table 7.

TABLE 7

Nonhematologic Adverse Events*

| | Q4W (n = 18) | | Q2W (n = 55) | |
|---|---|---|---|---|
| | All | Grade 3/4 | All | Grade 3/4 |
| Nausea | 50% | 0 | 56% | 2% |
| Vomiting | 22% | 0 | 18% | 0 |
| Anorexia | 22% | 0 | 27% | 0 |
| Neuropathy** | 22% | 0 | 22% | 0 |
| Asthenia | 17% | 0 | 36% | 2% |
| Alopecia | 17% | NA | 31% | NA |
| Fatigue | 17% | 0 | 7% | 0 |
| Creatinine Increased*** | 11% | 0 | 20% | 0 |
| Diarrhea | 17% | 0 | 9% | 0 |
| Dizziness | 0 | 0 | 16% | 0 |
| Stomatitis | 0 | 0 | 9% | 4% |
| Erythema | 6% | 0 | 4% | 0 |
| Tinnitus | 0 | 0 | 6% | 0 |

*Drug-related events that occurred in more than 1 patient.
**Neuropathy includes neuropathy, peripheral sensory neuropathy, neuropathy peripheral, and polyneuropathy
***When assessed and graded using lab values, 28% on the Q4W arm and 29% on the Q2W arm had grade 1 creatinine levels. 1 patient each on the Q2W arm had grade 1 and grade 2. There were no grade 3 or 4 creatinine levels.

The cardiac and stomatitis events were attributed to the 5-FU component. No Grade 2 or higher neuropathy has been reported, even for four patients who have received a cumulative picoplatin dose of greater than about 900 mg/m$^2$, e.g., from about 902-1871 mg/m$^2$, a surprising and unexpected result, particularly in view of a high incidence of moderate to severe neuropathy observed at comparable doses of oxaliplatin. Picoplatin can be safely administered with FU and LV without the dose limiting neuropathy associated with FOLFOX.

In Schedule A (picoplatin q 2 week), the preferred dosage range is about 45-120 mg/m$^2$, e.g., doses of 45 to 105 mg/m$^2$, e.g., 85 mg/m$^2$.

In Schedule B (picoplatin q 4 week), the preferred dose can be higher, e.g., about 120-210 mg/m$^2$, e.g., 120-180 mg/m$^2$, e.g., 150 mg/m$^2$. A lower dose can also be administered, e.g., at 45-90 mg/m$^2$, e.g., 60 mg/m$^2$.

Of 73 evaluated subjects evaluated by CT scan there have been 19 confirmed partial responses and one complete response (unconfirmed). Fifty-five of the subjects of the Q2 week schedule have been evaluated and 13 partial responses were observed (24%). Surprisingly, some patients in cohort A1 (45 mg/m$^2$) showed a partial response. Eighteen of 18 subjects in the Q4 week schedule have been evaluated and 6 partial responses were observed (33%). These results are summarized on Table 8.

TABLE 8

Tumor Assessment (RECIST)

| | Q4W (n = 18) | Q2W (n = 55) |
|---|---|---|
| Partial Response | 6 (33%) | 13 (24%) |
| Stable Disease | 6 (33%) | 28 (51%) |
| Disease Control (PR + SD) | 12 (67%) | 41 (75%) |
| Progressive Disease | 6 (33%) | 10 (18%) |
| Not evaluable | 0 | 4 (7%) |

One patient was a 47 year-old woman with CRC diagnosed 12, Nov. 2007. She was treated with laparotomy and sigmoidostomy; four hepatic metastases were present, the largest was (31 mm). After 42 weeks of FOLPI, repeat spiral CT showed complete response, confirmed. At that time the investigator removed the patient from study for resection of her primary lesion.

Phase II Study

Randomized Phase II study of picoplatin in combination with 5-fluorouracil and leucovorin (FOLPI) as a neuropathy-sparing alternative to mFOLFOX-6 as first line therapy for colorectal cancer. A randomized, controlled study comparing the safety and efficacy of Q4W FOLPI (FOLPI with a 4 week dosing interval for picoplatin) at the picoplatin maximum tolerated dose (MTD) of 150 mg/m$^2$ in comparison with an mFOLFOX-6 regimen of 85 mg/m$^2$ oxaliplatin Q2W in combination with 5-FU and leucovorin in patients with metastatic CRC and no prior chemotherapy was carried out. Efficacy was assessed by objective tumor response using RECIST), progression-free survival, and overall survival. The safety of each regimen was evaluated based on the incidence of adverse effects. Peripheral neuropathy was assessed by 3 methods: investigator (using CTCAE), blinded independent neurologist and patient assessment (FACT; neurotoxicity questionnaire). The independent neurologist blinded to the treatment assignment assessed peripheral neuropathy using the following scale: 0: none, i.e., no neurosensory symptoms; 1: paresthesias, dysesthesias that interfere with function but not activities of daily living and persist between cycles; 3: paresthesias, dysesthesias with pain or functional impairment that also interfere with activities of daily living and persist between cycles; and 4: paresthesias, dysesthesias that are persistent and are disabling or life threatening.

Study Demographics, are shown below on Table 9. Each arm of the study was comparable in size, and of comparable median age.

TABLE 9

Demographics

| | | FOLPI N = 51 | mFOLFOX-6 N = 50 |
|---|---|---|---|
| Age (in years) | Median (range) | 59 (25-78) | 62 (34-81) |
| Age Group | <65 years | 35 (71%) | 27 (54%) |
| | ≧65 years | 15 (29%) | 23 (46%) |
| ECOG PS | 0 | 5 (10%) | 10 (20%) |
| | 1 | 46 (90%) | 40 (80%) |
| Adjuvant Therapy | Yes | 4 (8%) | 5 (10%) |
| Original Site of Disease | Colon | 21 (41%) | 36 (72%) |
| | Rectum | 27 (53%) | 11 (22%) |
| | Colon + Rectum | 3 (6%) | 3 (6%) |
| Number of Metastatic Sites | Median (range) | 2 (1-6) | 2 (1-6) |
| Sites of Metastatic Disease | Liver | 43 (86%) | 43 (84%) |
| | Lymph nodes | 22 (43%) | 19 (38%) |
| | Lung | 20 (39%) | 15 (30%) |
| | Peritoneum/pelvic/ | 11 (22%) | 10 (20%) |

TABLE 9-continued

Demographics

|  | FOLPI N = 51 | mFOLFOX-6 N = 50 |
|---|---|---|
| abdominal | | |
| Bone | 4 (8%) | 1 (2%) |
| Ascites | 4 (8%) | 1 (2%) |
| Skin/soft tissue | 1 (2%) | 1 (2%) |
| Pleural Effusion | 0 | 2 (4%) |
| Other | 9 (18%) | 9 (18%) |

Results 101 pts were randomized (51 to FOLPI, 50 to FOLFOX-6). Pts have received a mean of 10 (median of 8), max 28 2-week cycles of FOLPI and a mean of 11 (median of 10), max 31 2-week cycles of FOLFOX-6. Median dose intensity of picoplatin (FOLPI)=28 mg/m$^2$/wk (range 9-70; mean mg/m$^2$/week of 29 (s.d. 6)); median relative dose intensity=83%. Median dose intensity of oxaliplatin (FOLFOX-6)=36 mg/m$^2$/wk (range 17-65; mean mg/m$^2$/week of 36 (s.d. 5)); median relative dose intensity=92%.

TABLE 10

Response

|  | FOLPI N = 51 | mFOLFOX-6 N = 50 |
|---|---|---|
| Complete Response | 2 (4%) | 3 (6%) |
| Partial Response | 9 (18%) | 11 (22%) |
| Stable Disease | 27 (53%) | 24 (48%) |
| Disease Control (PR + CR + SD) | 38 (75%) | 38 (76%) |
| Progressive Disease | 8 (16%) | 9 (18%) |
| Not evaluable | 5 (10%) | 3 (6%) |

Median progression free response (PFS) for FOLPI is 6.8 months (95% CI: 5.2, 7.4) and 7.0 months for FOLFOX (95% CI: 4.4, 8.5).

One patient was a 70 year-old woman with diagnosed CRC. She was treated with a/p resection and presented with a 20-mm hepatic metastasis. After 8 weeks of FOLPI treatment, repeat spiral CT was interpreted by the PI as complete response. Independent radiologist evaluation was partial response, confirmed.

Another patient was a 66 year old Caucasian female with history of ischemic cardiac disease, hypertension and stroke, who underwent sigmoidectomy for colorectal cancer. Two hepatic metastases measuring a total of 47 mm were present when she started treatment with FOLPI. To date, she has completed >25 two-week cycles of treatment over 1 year, achieving complete response by cycle 17 (approximately 34 weeks) after starting treatment. Adverse events of included grade 3 thrombocytopenia and neutropenia, and alopecia. She continued on treatment in complete response.

Neurotoxicity (peripheral neuropathy) was observed in 60% of pts on FOLFOX (16% G ¾) and 29% of pts on FOLPI (no G ¾). Most frequent G ¾ AEs on FOLPI were neutropenia (60%), thrombocytopenia (40%) and anemia (14%). In the FOLFOX arm, other than neuropathy, the most frequent G ¾ AEs were neutropenia (20%) and thrombocytopenia (12%). Disease control (CR+PR+SD) was 75% for FOLPI and 76% for FOLFOX. In the FOLPI arm there were 2 CR (4%) and 9 PR (18%). In the FOLFOX arm there were 3 CR (6%) and 11 PR (22%).

TABLE 10

Hematological Toxicity*

|  | Grade | FOLPI N = 50 | mFOLFOX-6 N = 49 |
|---|---|---|---|
| ANC | 1 | 2 (4%) | 8 (16%) |
|  | 2 | 8 (16%) | 6 (12%) |
|  | 3 | 15 (30%) | 9 (18%) |
|  | 4 | 17 (34%) | 3 (6%) |
| Platelets | 1 | 13 (26%) | 23 (47%) |
|  | 2 | 10 (20%) | 2 (4%) |
|  | 3 | 18 (36%) | 5 (10%) |
|  | 4 | 5 (10%) | 4 (8%) |
| Hemoglobin | 1 | 14 (28%) | 24 (49)% |
|  | 2 | 19 (38%) | 14 (29%) |
|  | 3 | 10 (20%) | 3 (6%) |
|  | 4 | 4 (8%) | 3 (6%) |

*1 patient had febrile neutropenia

TABLE 11

Nonhematologic Adverse Events

|  | FOLPI N = 51 | mFOLFOX-6 N = 50 |
|---|---|---|
| Nausea | 43% | 54% |
| Asthenia | 37% | 36% |
| Vomiting | 28% | 28% |
| Neuropathy | 29% | 60% |
| Anorexia | 18% | 12% |
| Diarrhea | 22% | 18% |
| Alopecia | 20% | 4% |
| Increase creatinine | 12% | 10% |

FOLPI and mFOLFOX-6 deliver almost identical dose intensities of platinum. Three measurements of neuropathy agree on the superiority of FOLPI as a neuropathy-sparing alternative to FOLFOX. The Q4W FOLPI regimen exhibits later and less frequent and severe neurotoxicity than does mFOLFOX-6, while producing comparable rates of progression free survival and disease control, such as partial response, complete response and stable disease. Neurotoxicity is not dose-limiting for the FOLPI regimen, and the Q4W FOLPI regimen has comparable non-neurological tolerability to mFOLFOX-6. Although thrombocytopenia and neutropenia (hematological toxicity) are more frequent and severe with FOLPI than with mFOLFOX-6, they are manageable, and the acute gastrointestinal toxicity of the two regimens, as well as ototoxicity, is similar. Thus, FOLPI is a neuropathy sparing alternative to mFOLFOX-6 as first-line therapy for colorectal cancer.

BIBLIOGRAPHY

1. Jemal et al., Cancer Statistics, 2004. CA Cancer J Clin 54(1): 8-29, 2004.
2. Hoff et al., Oncology (Huntingt) 18(6): 705-708, 2004.
3. Meyerhardt et al., N Engl J Med 352(5): 476-87, 2005.
4. Penland et al., Oncology (Huntingt) 18(6): 715-722, 2004.
5. Saltz et al., N Engl J Med, 343(13): 905-14, 2000.
6. Tournigand et al., J Clin Oncol, 22(2): 229-37, 2004.
7. de Gramont et al., J Clin Oncol, 18(16): 2938-47, 2000.
8. Rothenberg et al., J Clin Oncol, 21(11): 2059-69, 2003.
9. Andre et al., N Engl J Med, 350(23): 2343-51, 2004.
10. Hwang et al., In: *Clinical Use of Oxaliplatin: Case Studies and Roundtable Discussion*, Editor Marshall J, CMP Healthcare Media, Oncology Publishing Group, Manhasset, N.Y. 2004.

11. Douillard, J Y, Schiller, J., Eur J Cancer 38(Suppl 8): S25-S31, 2002.
12. Beale, P, et al., Br J Cancer 88(7): 1128-1134, 2003.
13. Raynaud F I, et al., Clin Cancer Res 3(11): 2063-2074, 1997.
14. Holford J, et al., Anticancer Drug Des 13(1): 1-18, 1998.
15. Holford J, et al., Br J Cancer 77(3): 366-373, 1998.
16. Rogers P, et al., Eur J Cancer 38(12):1653-1660, 2002.
17. Sharp S Y, et al., Eur J Cancer 38(17):2309-15, 2002.
18. Plasencia C, et al., Invest New Drugs 22(4):399-409, 2004.
19. Murakami H, et al., Eur J Cancer 38(Suppl 8): S1-S5, 2002
20. Giaccone G, et al., Eur J Cancer 38 (Suppl 8): S19-S24, 2002.
21. Gore M E, et al., Eur J Cancer 38(18): 2416-2420, 2002.
22. Treat J, et al., Eur J Cancer 38(Suppl 8): S13-18, 2002.
23. Perez RP, et al., Eur J Cancer 34(10): 1535-42, 1998.
24. Gelmon K A, et al., Ann Oncol 15(7):1115-22, 2004.
25. Gelmon K A, et al., National Cancer Institute of Canada—Clinical Trials Group trial, IND 129. Ann Oncol 14: 543-548, 2003.
26. Therasse P, et al., New Guidelines to Evaluate the Response to Treatment in Solid Tumors. European Organization for Research and Treatment of Cancer, National Cancer Institute of the United States, National Cancer Institute of Canada. J Natl Cancer Inst 92(3): 205-216, 2000.

U.S. Ser. No. 61/055,071, filed May 21, 2008;
U.S. Ser. No. 61/027,387, filed Feb. 8, 2008:
PCT/US2009/000770, filed Feb. 6, 2009;
U.S. Ser. No. 61/027,382, filed Feb. 8, 2008;
PCT/US2009/000773, filed Feb. 6, 2009;
U.S. Ser. No. 61/027,360, filed Feb. 8, 2008;
PCT/US2009/000750, filed Feb. 6, 2009;
U.S. Ser. No. 11/982,841, filed Nov. 5, 2007;
U.S. Ser. No. 61/170,487, filed Apr. 17, 2009;
PCT/US2008/008076; and
PCT/US2008/008669.

All publications, patents and patent applications cited herein are incorporated by reference herein.

What is claimed is:

1. A method of treatment of colorectal cancer, comprising: administering to a patient afflicted with colorectal cancer effective amounts of a combination of picoplatin, 5-fluorouracil (5-FU) and leucovorin, wherein the picoplatin, 5-FU and leucovorin are administered intravenously at least twice at intervals of about two weeks, wherein the amount of picoplatin is about 40-60 mg/m$^2$ every two weeks.

2. The method of claim 1 wherein the patient has not previously been treated for metastatic disease.

3. The method of claim 2 wherein the patient has not previously been treated systemically for metastatic disease.

4. The method of claim 1 wherein the colorectal cancer comprises metastatic sites.

5. The method of claim 4 wherein the treatment is curative of colorectal cancer metastases.

6. The method of claim 1 wherein the primary tumor is resected or debulked following administration of the picoplatin, the 5-FU and the leucovorin.

7. The method of claim 1 wherein the patient has previously had surgery to resect or de-bulk a colorectal tumor.

8. The method of claim 1 wherein the administration is effective to prevent or delay development or metastasis of the colorectal cancer.

9. The method of claim 1 wherein the picoplatin, when administered, and the leucovorin are administered substantially concurrently.

10. The method of claim 1 wherein the picoplatin, when administered, and the leucovorin are administered simultaneously.

11. The method of claim 1 wherein the 5-FU is administered following the administration of the picoplatin and the leucovorin.

12. The method of claim 1 wherein the leucovorin is administered at a dosage of about 400 mg/m$^2$.

13. The method of claim 1 wherein the 5-FU is administered at a total dosage per dosing of about 2000-3000 mg/m$^2$.

14. The method of claim 1 wherein the picoplatin is administered at a cumulative dosage of at least about 900 mg.

15. The method of claim 14 wherein the picoplatin is administered at a cumulative dosage of about 900-2000 mg/m$^2$.

16. The method of claim 1 wherein the picoplatin is administered at least once at a dosage of about 40-45 mg/m$^2$.

17. The method of claim 1 further comprising administration of a 5-HT$_3$ receptor antagonist.

18. The method of claim 1 comprising administering the picoplatin in a dosage form comprising an isotonic solution comprising:
(a) water;
(b) a tonicity adjuster; and
(c) about 0.5 mg/mL dissolved picoplatin.

* * * * *